(12) United States Patent
Kick et al.

(10) Patent No.: US 8,901,106 B2
(45) Date of Patent: Dec. 2, 2014

(54) IMIDAZOLE PRODRUG LXR MODULATORS

(75) Inventors: Ellen K. Kick, Ewing, NJ (US);
Michael J. Hageman, Pennington, NJ (US); Victor R. Guarino, Pennington, NJ (US); Ching-Chiang Su, Yardley, PA (US); Chenkou Wei, Princeton Junction, NJ (US); Jayakumar S. Warrier, Bangalore (IN); Satheesh Nair, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/006,980

(22) PCT Filed: Mar. 26, 2012

(86) PCT No.: PCT/US2012/030499
§ 371 (c)(1),
(2), (4) Date: Sep. 24, 2013

(87) PCT Pub. No.: WO2012/135082
PCT Pub. Date: Oct. 4, 2012

(65) Prior Publication Data
US 2014/0018321 A1    Jan. 16, 2014

Related U.S. Application Data

(60) Provisional application No. 61/467,404, filed on Mar. 25, 2011.

(51) Int. Cl.
*C07D 233/64* (2006.01)
*A61K 31/4174* (2006.01)
*A61K 45/06* (2006.01)
*A61K 31/675* (2006.01)
*C07F 9/6506* (2006.01)
*C07F 9/12* (2006.01)

(52) U.S. Cl.
CPC .............. *C07D 233/64* (2013.01); *A61K 45/06* (2013.01); *A61K 31/675* (2013.01); *A61K 31/4174* (2013.01); *C07F 9/12* (2013.01); *C07F 9/65061* (2013.01)
USPC ........... 514/94; 514/400; 548/119; 548/346.1

(58) Field of Classification Search
CPC . A61K 31/4174; A61K 31/675; A61K 45/06; C07D 233/64; C07F 9/12; C07F 9/6506
USPC .......................... 514/94, 400; 548/119, 346.1
See application file for complete search history.

(56) References Cited

U.S. PATENT DOCUMENTS

| 8,569,352 B2 | 10/2013 | Busch et al. |
| 8,618,154 B2 | 12/2013 | Busch et al. |
| 2010/0075964 A1 | 3/2010 | Busch et al. |
| 2012/0071534 A1 | 3/2012 | Busch et al. |

FOREIGN PATENT DOCUMENTS

WO    WO 2010/138598    12/2010

OTHER PUBLICATIONS

Dhareshwar, S.S. et al., "Prodrugs of Alcohols and Phenols", Biotechnology: Pharmaceutical Aspects, Prodrugs Challenges and Rewards, Part 1, pp. 32-99 (2007).
Fleisher, D. et al., "Improved oral drug delivery: solubility limitations overcome by the use of prodrugs", Advanced Drug Delivery Reviews, vol. 19, pp. 115-130 (1996).
Rautio, J. et al., "Prodrugs: design and clinical applications", Nature Reviews: Drug Discovery, vol. 7, No. 3, pp. 255-270 (2008).

*Primary Examiner* — San-Ming Hui
*Assistant Examiner* — Kathrien Cruz
(74) *Attorney, Agent, or Firm* — Mary K. VanAtten

(57) ABSTRACT

Imidazole prodrugs, pharmaceutically acceptable salts, or isomers thereof, of the invention are disclosed, which are useful as modulators of the activity of liver X receptors (LXR). Pharmaceutical compositions containing the compounds and methods of using the compounds are also disclosed.

14 Claims, 9 Drawing Sheets

FIG. 1

Solubility profiles of 2-(2-(1-(2,6-dichlorophenyl)-1-methylethyl)-1-(3,3'-difluoro-4'-(hydroxymethyl)-5'-(methylsulfonyl)-4-biphenylyl)-1*H*-imidazol-4-yl)-2-propanol and (4'-(2-(1-(2,6-dichlorophenyl)-1-methylethyl)-4-(1-hydroxy-1-methylethyl)-1*H*-imidazol-1-yl)-3,3'-difluoro-5-(methylsulfonyl)biphenyl-4-yl)methyl dihydrogen phosphate

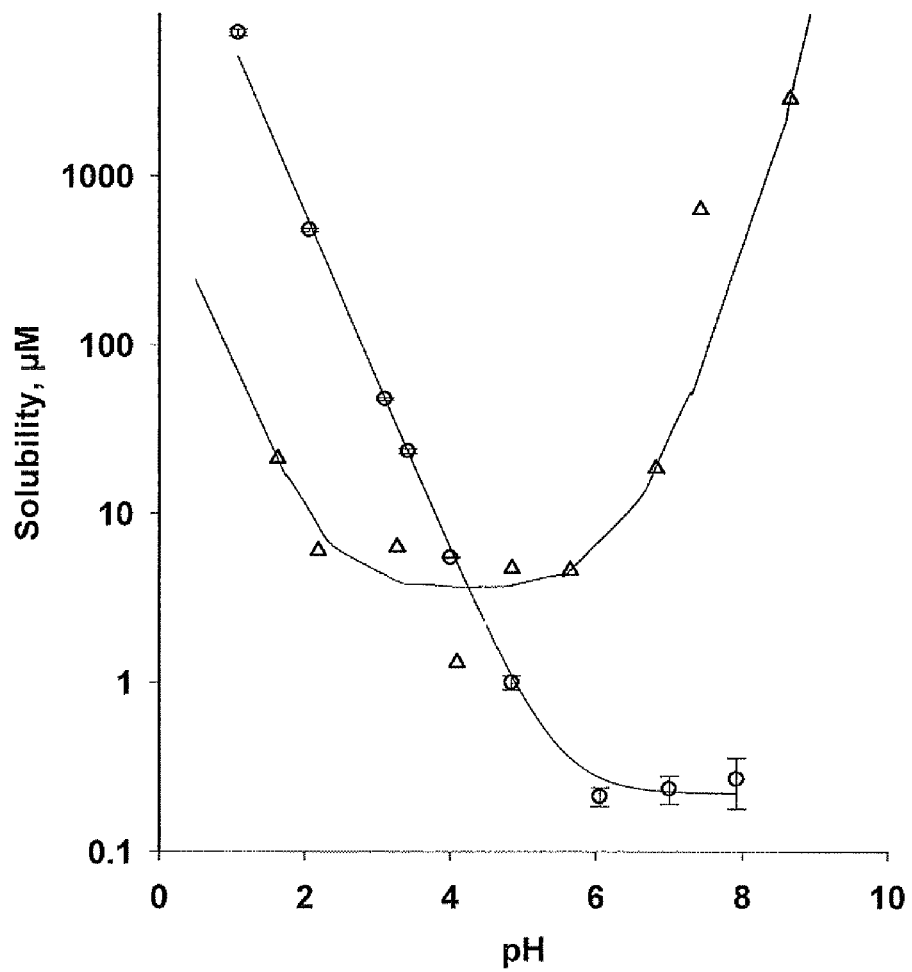

○ 2-(2-(1-(2,6-dichlorophenyl)-1-methylethyl)-1-(3,3'-difluoro-4'-(hydroxymethyl)-5'-(methylsulfonyl)-4-biphenylyl)-1H-imidazol-4-yl)-2-propanol △ (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate Experimental powder X-ray diffraction pattern of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2(hydroxymethyl)-1,3-propanediol) ethanolate salt), Form E-1

Experimental and simulated powder X-ray diffraction patterns of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate, Form H-1

DSC of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt), Form E-1

TGA of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt), Form E-1

Moisture-Sorption Isotherm of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate, Form H-1

¹³C CPMAS ssNMR Spectrum of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt), Form E-1

13C CPMAS ssNMR Spectrum of (4'-(2-(2-(2,6-dichlorophenyl)propan-2-yl)-4-(2-hydroxypropan-2-yl)-1*H*-imidazol-1-yl)-3,3'-difluoro-5-(methylsulfonyl)biphenyl-4-yl)methyl dihydrogen phosphate, Form H-1

19F ssNMR Spectrum of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt), Form E-1

IMIDAZOLE PRODRUG LXR MODULATORS

This application is a 371 application of PCT/US2012/030499, filed Mar. 26, 2012 which claims priority from U.S. Provisional Application Ser. No. 61/467,404 filed Mar. 25, 2011 which are incorporated by reference herein in their entirety.

FIELD OF THE INVENTION

The present invention provides for prodrug imidazole compounds useful as modulators of nuclear receptors, including liver X receptor (LXR), and to pharmaceutical compositions containing such compounds. The present invention further provides for methods of using such compounds in the treatment and prevention of diseases or disorders mediated by or in which nuclear receptor activity, including LXR and/or orphan nuclear receptor activity.

BACKGROUND OF THE INVENTION

Nuclear receptors are a superfamily of regulatory proteins that are structurally and functionally related and are receptors for, e.g., steroids, retinoids, vitamin D and thyroid hormones (see, e.g., Evans, *Science,* 240:889-895 (1988)). These proteins bind to cis-acting elements in the promoters of their target genes and modulate gene expression in response to ligands for the receptors.

Nuclear receptors can be classified based on their DNA binding properties (see, e.g., Evans, supra, and Glass, *Endocr. Rev.,* 15:391-407 (1994)). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptors or PPARs) and ecdysone, bind to HREs as heterodimers with a common partner, the retinoid X receptors (i.e., RXRs, also known as the 9-cis retinoic acid receptors; see, e.g., Levin et al., *Nature,* 355:359-361 (1992) and Heyman et al., *Cell,* 68:397-406 (1992)).

RXRs are unique among the nuclear receptors in that they bind DNA as a homodimer and are required as a heterodimeric partner for a number of additional nuclear receptors to bind DNA (see, e.g., Mangelsdorf et al., *Cell,* 83:841-850 (1995)). The latter receptors, termed the class II nuclear receptor subfamily, include many which are established or implicated as important regulators of gene expression. There are three RXR genes (see, e.g., Mangelsdorf et al., *Genes Dev.,* 6:329-344 (1992)), coding for RXRα, -β, and -γ, all of which are able to heterodimerize with any of the class II receptors, although there appear to be preferences for distinct RXR subtypes by partner receptors in vivo (see, e.g., Chiba et al., *Mol. Cell. Biol.,* 17:3013-3020 (1997)). In the adult liver, RXRα is the most abundant of the three RXRs (see, e.g., Mangelsdorf et al., *Genes Dev.,* 6:329-344 (1992)), suggesting that it might have a prominent role in hepatic functions that involve regulation by class II nuclear receptors. See also, Wan et al., *Mol. Cell. Biol.,* 20:4436-4444 (2000).

$LXR_\alpha$ is found predominantly in the liver, with lower levels found in kidney, intestine, spleen and adrenal tissue (see, e.g., Willy et al., *Genes Dev.,* 9(9):1033-1045 (1995)). $LXR_\beta$ is ubiquitous in mammals and was found in nearly all tissues examined LXRs are activated by certain naturally occurring, oxidized derivatives of cholesterol (see, e.g., Lehmann et al., *J. Biol. Chem.,* 272(6):3137-3140 (1997)). $LXR_\alpha$ is activated by oxycholesterol and promotes cholesterol metabolism (Peet et al., *Cell,* 93:693-704 (1998)). Thus, LXRs appear to play a role in, e.g., cholesterol metabolism (see, e.g., Janowski et al., *Nature,* 383:728-731 (1996)).

The nuclear receptor LXR plays a critical role in coordinate control of bile acid, cholesterol, and triglyceride metabolism to maintain lipid homeostasis. LXRs and bile acid/oxysterol-regulated genes are potential targets for developing drug therapies for lowering serum cholesterol and treating cardiovascular and liver diseases. Compounds with activity at LXR can have profound effects on lipid homeostasis, and can more effectively control disease or disorders in which LXR is implicated. This is accomplished through regulation of multiple genes involved in cholesterol homeostasis including Cyp7a1, a member of the cytochrome p450 family of enzymes and the rate limiting step in bile acid synthesis, as well as the ABC membrane transporters ABCA1, ABCG1, ABCG5, and ABCG8. ABCA1 is critical in the efflux of cholesterol and phospholipids to lipid-poor lipoproteins such as ApoA-I thus contributing to an increase in plasma HDL levels. In addition, ABCG5 and ABCG8 appear to mediate decreased intestinal absorption of cholesterol and facilitate cholesterol efflux from liver cells into the bile. Unfortunately, in addition to the anti-atherogenic effect of LXR agonists, studies in cell culture and animal model systems have demonstrated that LXR agonists increase plasma triglyceride levels and hepatic lipogenesis and promote the increased production of VLDL lipoprotein particles. Schultz et al., *Genes Dev.,* 14:2831-2838 (2000); Repa et al., *Genes Dev.,* 14:28119-2830 (2000). Strategies to minimize the undesirable lipid effects include identifying $LXR_\beta$ selective compounds that are also partial agonists. Partial agonists can display tissue-specific activation or repression of nuclear receptors, as was demonstrated for the anti-estrogen tamoxifen, which functions as an antagonist of estrogen signaling in breast tissue and an agonist in the uterus. Characterization of LXR isoform-specific null mice indicate that $LXR_\alpha$ is the predominant mediator of LXR activity in the liver. In macrophages, however, $LXR_\beta$ alone is sufficient to mediate the effects of LXR ligands on target gene expression. Therefore compounds with limited $LXR_\alpha$ activity should have anti-atherogenic activity while limiting unwanted hepatic effects.

Nuclear receptor activity has been implicated in a variety of diseases and disorders, including, but not limited to, hypercholesterolemia (see, e.g., PCT Publication No. WO 00/57915), osteoporosis and vitamin deficiency (see, e.g., U.S. Pat. No. 6,316,503), hyperlipoproteinemia (see, e.g., PCT Publication No. WO 01/60818), hypertriglyceridemia, lipodystrophy, hyperglycemia and diabetes mellitus (see, e.g., PCT Publication No. WO 01/82917), atherosclerosis and gallstones (see, e.g., PCT Publication No. WO 00/37077), disorders of the skin and mucous membranes (see, e.g., U.S. Pat. Nos. 6,184,215 and 6,187,814, and PCT Publication No. WO 98/32444), acne (see, e.g., PCT Publication No. WO 00/49992), and cancer, Parkinson's disease and Alzheimer's disease (see, e.g., PCT Publication No. WO 00/17334). Activity of nuclear receptors, including LXRs, FXR and PPAR, and orphan nuclear receptors, has been implicated in physiological processes including, but not limited to, bile acid biosynthesis, cholesterol metabolism or catabolism, and modulation of cholesterol 7.alpha.-hydroxylase gene (CYP7A1) transcription (see, e.g., Chiang et al., *J. Biol. Chem.,* 275:10918-10924 (2000)), HDL metabolism (see, e.g., Urizar et al., *J. Biol. Chem.,* 275:39313-39317 (2000) and PCT Publication No. WO 01/03705), and increased cholesterol efflux and increased expression of ATP binding cassette transporter protein (ABC1) (see, e.g., PCT Publication No. WO 00/78972).

Thus, we recognized that there is a need for compounds, compositions and methods of modulating the activity of the LXR nuclear receptors in ways that separate the desirable effects on cholesterol metabolism and atherogenesis from increased plasma triglyceride levels and an increase in hepatic lipogenesis. Although full agonists of LXR cause both the desirable and undesirable effects, the present invention describes compounds that have a beneficial separation between the two, and thus have an improved therapeutic index between increased reverse cholesterol transport and detrimental effects on plasma triglycerides and LDL-cholesterol.

SUMMARY OF THE INVENTION

In one embodiment, the present invention comprises compounds or an individual isomer or mixture of isomers, an isotope or a pharmaceutically acceptable salt thereof, which are useful as modulators of the activity of liver X receptors (LXRs).

Compounds for use in compositions and methods for modulating the activity of nuclear receptors are provided. In particular, compounds of the invention are prodrugs of compounds that are useful for modulating the liver X receptors, $LXR_\alpha$ and $LXR_\beta$, and in particular, $LXR_\beta$.

Furthermore, compounds of the present invention show unexpected advantages over compounds previously disclosed in the art, such as those disclosed in PCT Publication No. WO 2010/138598. The present prodrug compounds have been shown to have a desirable pH dependent absorption and therefore improved bioavailability of the parent compound. Particularly, the compounds of the present invention have been shown to increase the bioavailability of 2-(2-(1-(2,6-dichlorophenyl)-1-methylethyl)-1-(3,3'-difluoro-4'-(hydroxymethyl)-5'-(methylsulfonyl)-4-biphenylyl)-1H-imidazol-4-yl)-2-propanol at elevated gastric pH (e.g., pH 7), for example, in dogs treated with famotidine. Such compounds should be more useful in the treatment, inhibition or amelioration of one or more diseases or disorders that are discussed herein.

Another embodiment of this invention is directed to methods of treating, inhibiting, or ameliorating the symptoms of a disease or disorder that is modulated or otherwise affected by LXR activity or in which LXR activity is implicated, comprising administering to a subject in need thereof a therapeutically effective amount of a compound of the present invention or an individual isomer or mixture of isomers or a pharmaceutically acceptable salt thereof.

Another embodiment of this invention is directed to methods of modulating cholesterol metabolism to a subject in need thereof, comprising administering an effective cholesterol metabolism-modulating amount of a compound of the present invention or an individual isomer or mixture of isomers or a pharmaceutically acceptable salt thereof.

Another embodiment of this invention is directed to methods of preventing or treating atherosclerosis in a subject in need thereof, comprising administering an effective cholesterol level-reducing amount of a compound of the present invention or an individual isomer or mixture of isomers or a pharmaceutically acceptable salt thereof.

Another embodiment of this invention is directed to methods of modulating LXR activity to a subject in need thereof, comprising contacting the nuclear receptor with a compound of the present invention or an individual isomer or mixture of isomers or a pharmaceutically acceptable salt thereof.

Another embodiment of this invention is directed to methods of treating, inhibiting or ameliorating one or more symptoms of hypocholesterolemia in a subject in need thereof, comprising administering a therapeutically effective amount of a compound of the present invention or an individual isomer or mixture of isomers or a pharmaceutically acceptable salt thereof.

Another embodiment of this invention is directed to methods of increasing cholesterol efflux from cells of a subject in need thereof, comprising administering an effective cholesterol efflux-increasing amount of a compound of the present invention or an individual isomer or mixture of isomers or a pharmaceutically acceptable salt thereof.

Another embodiment of this invention is directed to methods of increasing the expression of ATP-Binding Cassette A1 (ABCA1) and ATP-Binding Cassette G1 (ABCG1) in the cells of a subject in need thereof, comprising administering an effective ABCA1 and ABCG1 expression-increasing amount of a compound of the present invention or an individual isomer or mixture of isomers or a pharmaceutically acceptable salt thereof.

Another embodiment of this invention is directed to methods of treating, inhibiting, or ameliorating one or more symptoms of a disease or disorder which is affected by cholesterol or bile acid levels, comprising administering to a subject in need thereof a therapeutically effective amount of a compound of the present invention or an individual isomer or mixture of isomers or a pharmaceutically acceptable salt thereof.

Another embodiment of this invention is directed to pharmaceutical compositions comprising a compound of the present invention or an individual isomer or mixture of isomers or a pharmaceutically acceptable salt thereof and at least one pharmaceutically acceptable carrier or excipient.

Another embodiment of this invention is directed to pharmaceutical compositions comprising a compound of the present invention or an individual isomer or mixture of isomers or a pharmaceutically acceptable salt thereof and at least one additional therapeutic agent. For example, at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as razaxaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

Another embodiment of this invention is directed to regulation of reverse cholesterol transport and inflammatory signaling pathways that are implicated in human disease pathology including atherosclerosis and associated diseases such as myocardial infarction and ischemic stroke in a subject in need thereof, comprising administering an effective reverse cholesterol transport and inflammatory signaling pathways regulating amount of a compound of the present invention or an individual isomer or mixture of isomers or a pharmaceutically acceptable salt thereof.

Another embodiment of this invention is directed to treatment of the metabolic syndrome which comprises a constellation of disorders of the body's metabolism including obesity, macular degeneration, hypertension, insulin resistance, and diabetes including treatment of diseases resulting from compromised metabolism and immunity including atherosclerosis and diabetes as well as autoimmune disorders and diseases in a subject in need thereof, comprising administering a therapeutically effective amount of a compound of the present invention or an individual isomer or mixture of isomers or a pharmaceutically acceptable salt thereof.

Another embodiment of this invention is directed to treatment of the atherosclerosis, insulin resistance, osteoarthritis, stroke, hyperglycemia, dyslipidemia, psoriasis, aged and UV skin wrinkling, diabetes, cancer, Alzheimer's disease, inflammation, immunological disorders, lipid disorders, obesity, macular degeneration, conditions characterized by a perturbed epidermal barrier function, conditions of disturbed differentiation or excess proliferation of the epidermis or mucous membrane, or cardiovascular disorders in a subject in need thereof, comprising administering a therapeutically effective amount of a compound of the present invention or an individual isomer or mixture of isomers or a pharmaceutically acceptable salt thereof.

DESCRIPTION OF THE DRAWINGS

FIG. 1. Solubility profiles of 2-(2-(1-(2,6-dichlorophenyl)-1-methylethyl)-1-(3,3'-difluoro-4'-(hydroxymethyl)-5'-(methylsulfonyl)-4-biphenylyl)-1H-imidazol-4-yl)-2-propanol, disclosed in PCT Publication No. WO 2010/138598, and (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate, Example 1 of the present invention.

DEFINITIONS

Figure 2:
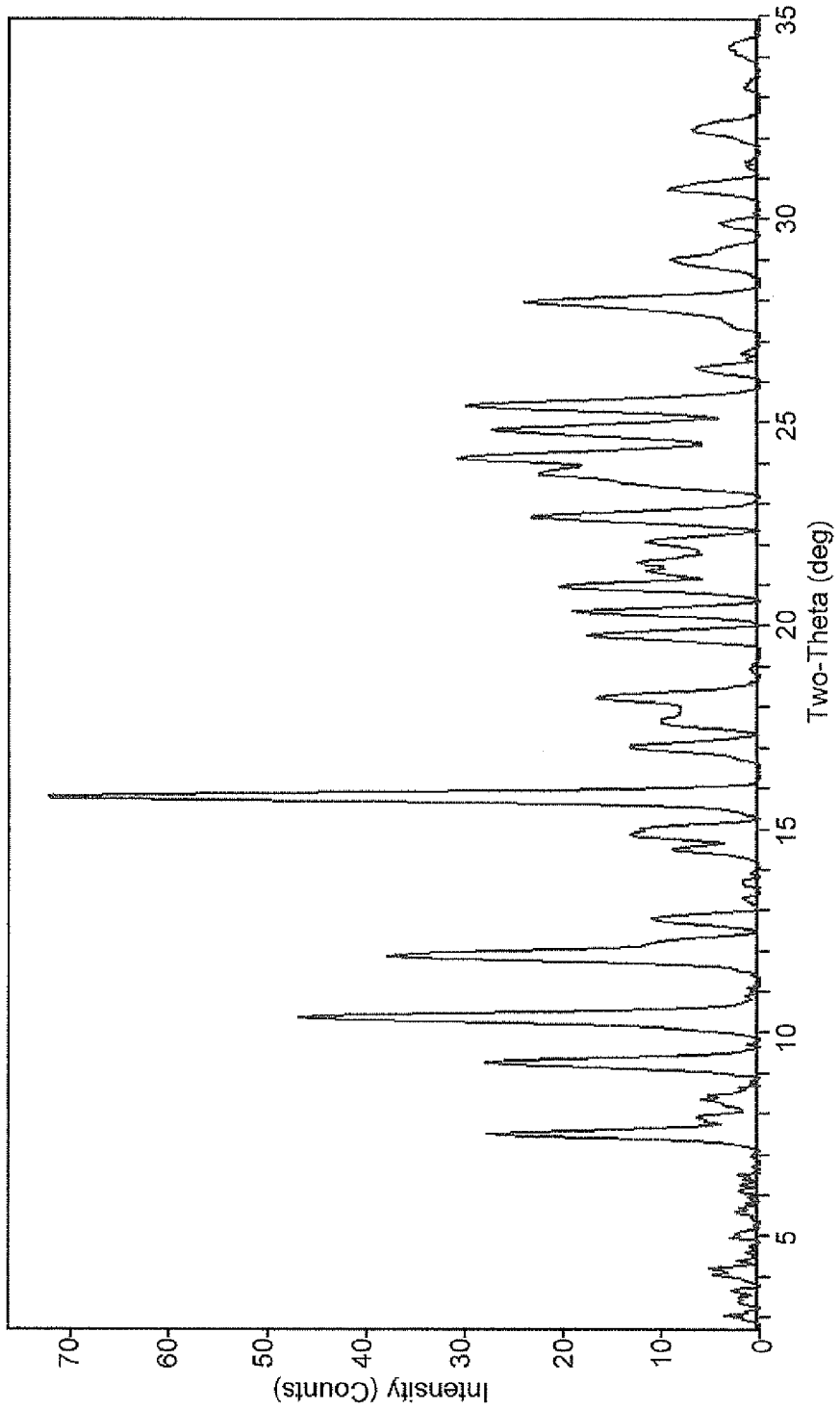
FIG. 2. Experimental powder X-ray diffraction pattern of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt), Form E-1.

"Nuclear receptor" refers to a receptor that activates or represses transcription of one or more genes in the nucleus (but can also have second messenger signaling actions), typically in conjunction with other transcription factors. The nuclear receptor is activated by the natural cognate ligand for the receptor. Nuclear receptors are ordinarily found in the cytoplasm or nucleus, rather than being membrane-bound. A nuclear receptor is a member of a superfamily of regulatory proteins that are receptors for various endogenous small molecules, e.g., steroids, retinoids, vitamin D and thyroid hormones. These proteins bind to cis-acting elements in the promoters of their target genes and modulate gene expression in response to a ligand therefore. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors is LXR.

"Liver X receptor" or "LXR" refers to a nuclear receptor implicated in cholesterol biosynthesis. As used herein, the term LXR refers to both $LXR_\alpha$ and $LXR_\beta$, two forms of the protein found in mammals. Liver X receptor-α or $LXR_\alpha$ refers to the receptor described in U.S. Pat. Nos. 5,571,696, 5,696,233 and 5,710,004, and Willy et al., *Genes Dev.*, 9(9): 1033-1045 (1995). Liver X receptor-β or $LXR_\beta$ refers to the receptor described in Peet et al., *Curr. Opin. Genet. Dev.*, 8(5):571-575 (1998); Song et al., *Ann. N.Y. Acad. Sci.*, 761: 38-49 (1995); Alberti et al., *Gene*, 243(1-2):93-103 (2000); and references cited therein; and in U.S. Pat. Nos. 5,571,696, 5,696,233 and 5,710,004.

The compounds of the present invention may form salts, preferably di-(2-amino-2-(hydroxymethyl)propanediol) ethanolate salts, which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound with an amount of acid or base, such as an equivalent amount, in a medium such as one in which the salt precipitates or in an aqueous medium followed by lyophilization. Exemplary salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like. Further exemplary salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present invention can modulate atherosclerosis by stimulating the removal of cholesterol from atherosclerotic lesions in a human.

"Treating" or "treatment" as used herein covers the treatment of a disease or disorder described herein, in a subject, preferably a human, and includes:

i. inhibiting a disease or disorder, i.e., arresting its development; or ii. relieving a disease or disorder, i.e., causing regression of the disorder.

"Subject" refers to a warm blooded animal such as a mammal, preferably a human, or a human child, which is afflicted with, or has the potential to be afflicted with one or more diseases and disorders described herein.

"Atherosclerosis" refers to a process whereby atherosclerotic plaques form within the inner lining of the artery wall leading to atherosclerotic cardiovascular diseases. Atherosclerotic cardiovascular diseases can be recognized and understood by physicians practicing in the relevant fields of medicine, and include without limitation, restenosis, coronary heart disease (also known as coronary artery disease or ischemic heart disease), cerebrovascular disease including ischemic stroke, multi-infarct dementia, and peripheral vessel disease, including intermittent claudication, and erectile dysfunction.

"Dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL).

"Cholesterol" refers to a steroid alcohol that is an essential component of cell membranes and myelin sheaths and, as used herein, incorporates its common usage. Cholesterol also serves as a precursor for steroid hormones and bile acids.

"Triglyceride(s)" or "TGs" refers to three fatty acid molecules esterified to a glycerol molecule and serve to store fatty acids which are used by muscle cells for energy production or are taken up and stored in adipose tissue.

"LXR" or "LXRs" refers to both $LXR_\alpha$ and $LXR_\beta$.

"$LXR_\alpha$" (LXR alpha) refers to all mammalian forms of such receptor including, for example, alternative splice isoforms and naturally occurring isoforms. Representative $LXR_\alpha$ species include, without limitation the rat (GENBANK® Accession No. NM_031627), mouse (GENBANK® Accession No. BC012646), and human (GENBANK® Accession No. U22662) forms of the receptor.

"$LXR_\beta$" (LXR beta) refers to all mammalian forms of such receptor including, for example, alternative splice isoforms and naturally occurring isoforms. Representative $LXR_\beta$ species include, without limitation the rat (GENBANK® Accession No. NM_031626), mouse (GENBANK® Accession No. NM_009473), and human (GENBANK® Accession No. U07132) forms of the receptor.

"Obese" and "obesity" refer to a Body Mass Index (BMI) greater than 27.8 $kg/m^2$ for men and 27.3 $kg/m^2$ for women (BMI equals weight $(kg)/(height)^2(m^2)$).

In addition, compounds of the present invention are, subsequent to their preparation, may be isolated and purified to obtain a composition containing an amount by weight equal to or greater than 99% of the compound ("substantially pure" compound), which is then used or formulated as described herein. Such "substantially pure" compounds of the present invention are also contemplated herein as part of the present invention.

To the extent that compounds of the present invention, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers.

The terms "including", "such as", "for example" and the like are intended to refer to exemplary embodiments and not to limit the scope of the present invention.

DETAILED DESCRIPTION OF THE INVENTION

It will be understood that any given exemplary embodiment can be combined with one or more additional exemplary embodiments.

In one aspect, the present invention comprises a compound, isotope, or pharmaceutically acceptable salt thereof, selected from:

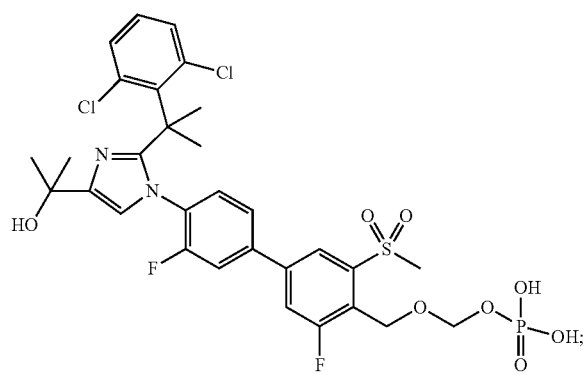
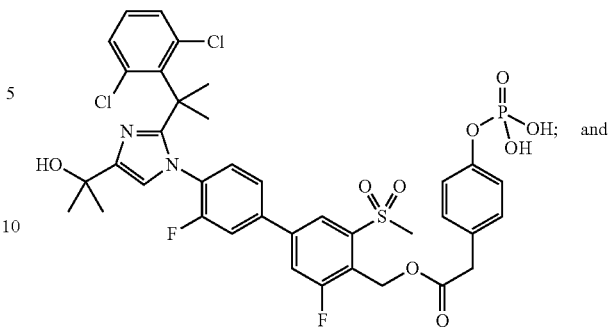
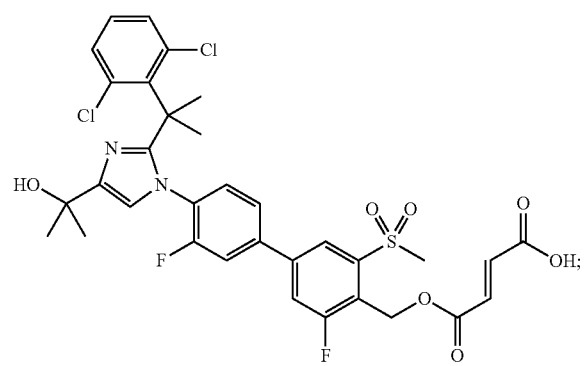 [SMILES: CC(C)(O)c1cn(-c2ccc(-c3cc(F)c(COC(=O)/C=C/C(=O)O)c(S(C)(=O)=O)c3)cc2F)c(C(C)(C)c2c(Cl)cccc2Cl)n1]
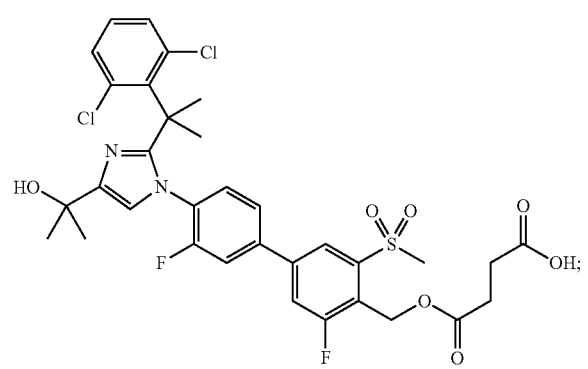 [SMILES: CC(C)(O)c1cn(-c2ccc(-c3cc(F)c(COC(=O)CCC(=O)O)c(S(C)(=O)=O)c3)cc2F)c(C(C)(C)c2c(Cl)cccc2Cl)n1]
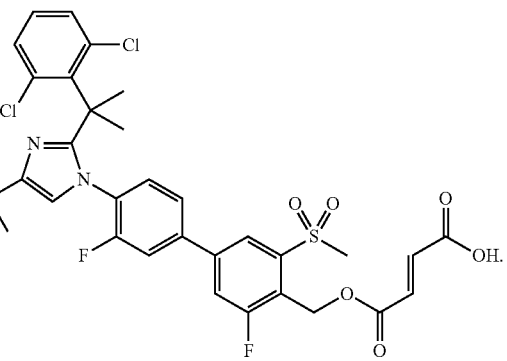
In one embodiment, the present invention comprises a compound, isotope, or pharmaceutically acceptable salt thereof, which is
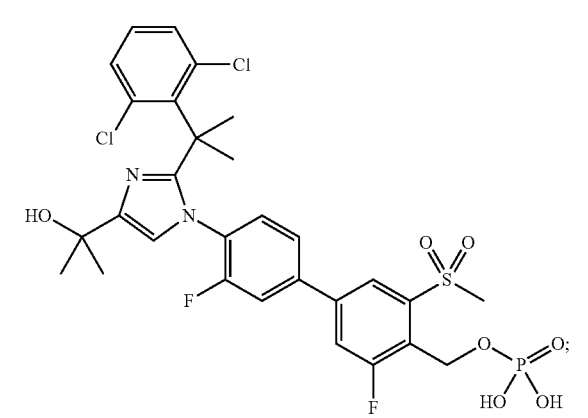 [SMILES: CC(C)(O)c1cn(-c2ccc(-c3cc(F)c(COP(=O)(O)O)c(S(C)(=O)=O)c3)cc2F)c(C(C)(C)c2c(Cl)cccc2Cl)n1]

In another embodiment, the present invention comprises a compound, isotope, or pharmaceutically acceptable salt thereof, which is

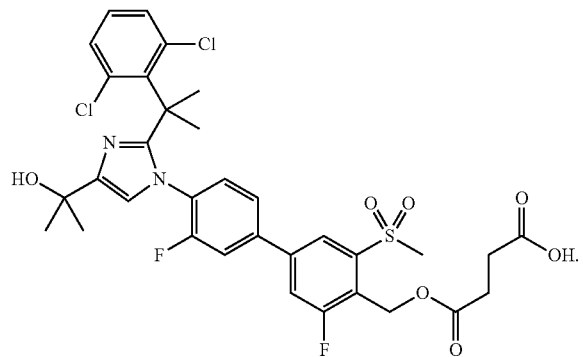

In yet another embodiment, the present invention comprises a compound, isotope, or pharmaceutically acceptable salt thereof, which is

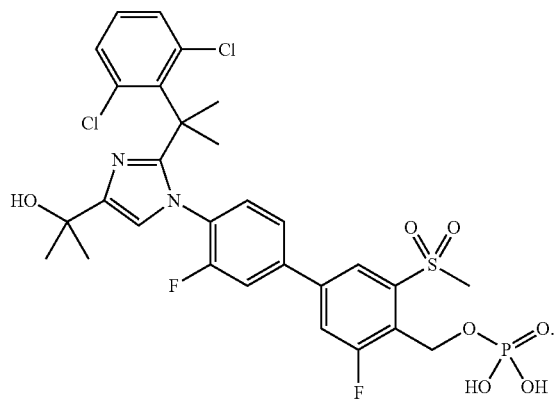

In yet another embodiment, the present invention comprises a compound, isotope, or pharmaceutically acceptable salt thereof, which is

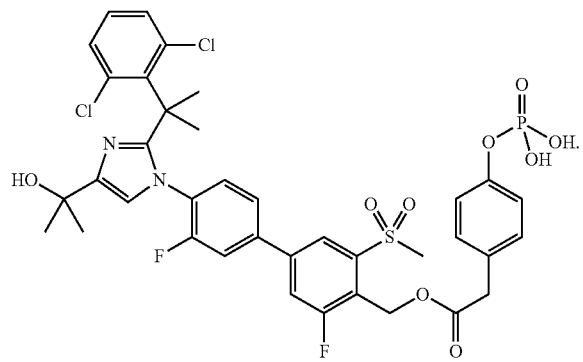 [SMILES: CC(C)(O)c1cn(-c2ccc(-c3cc(F)c(COC(=O)Cc4ccc(OP(=O)(O)O)cc4)c(S(C)(=O)=O)c3)cc2F)c(C(C)(C)c2c(Cl)cccc2Cl)n1]

In yet another embodiment, the present invention comprises a pharmaceutically acceptable salt, preferably, a di-(2-amino-2-(hydroxymethyl)propanediol) ethanolate salt, of a compound of the present invention.

In addition, compounds of the present invention, preferably, a compound selected from Examples 1, 3, 4, 6 and 7, more preferably, Examples 1, 3, and 4, and Forms E-1 and H-1, are, subsequent to their preparation, preferably isolated and purified to obtain a composition containing an amount by weight equal to or greater than 99% of said compound ("substantially pure" compound), which is then used or formulated as described herein. Such "substantially pure" compounds of the present invention, preferably Examples 1, 3, 4, 6 and 7, more preferably, Examples 1, 3, and 4, and Forms E-1 and H-1, are also contemplated herein as part of the present invention.

All stereoisomers of the compounds of the instant invention are contemplated, either in admixture or in pure or substantially pure form. The compounds of the present invention can have asymmetric centers at any of the sulfur or carbon atoms including any one of the R substituents and/or exhibit polymorphism. Consequently, compounds of the present invention can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^{2}H$ and $^{3}H$, carbon such as $^{11}C$, $^{13}C$, and $^{14}C$, chlorine, such as $^{36}Cl$, fluorine such as $^{18}F$, iodine, such as $^{123}I$ and $^{125}I$, nitrogen, such as $^{13}N$ and $^{15}N$, oxygen, such as $^{15}O$, $^{17}O$, and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^{3}H$, and carbon-14, $^{14}C$, are particularly useful for this purpose in view of their ease of incorporation and ready means of detection. Substitution with heavier isotopes such as deuterium, $^{2}H$, may afford certain therapeutic advantages resulting from greater metabolic stability, for example, increase in vivo half-life or reduced dosage requirements, and hence may be preferred in some circumstances. Substitution with positron emitting isotopes, such as $^{11}C$, $^{18}F$, $^{15}O$, and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

As used herein "solvate" refers to a crystalline form of a molecule, atom, and/or ions that further contains molecules of a solvent or solvents incorporated into the crystalline structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate.

The names used herein to characterize a specific form, e.g., "E-1" or "H-1", should not be considered limiting with respect to any other substance possessing similar or identical physical and chemical characteristics, but rather it should be understood that these designations are mere identifiers that should be interpreted according to the characterization information also presented herein.

The present invention provides, at least in part, crystalline forms of the free acid of (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate, as a novel material, in particular in a pharmaceutically acceptable form. In certain preferred embodiments, crystalline forms of the free acid are in substantially pure form. Preferred embodiments of crystalline forms of the free acid are disclosed as the di-(2-amino-2-(hydroxymethyl)propanediol) ethanolate salt or E-1 Form and the H-1 Form, respectively.

As used herein "polymorph" refers to crystalline forms having the same chemical composition but different spatial arrangements of the molecules, atoms, and/or ions forming the crystal.

As used herein "amorphous" refers to a solid form of a molecule, atom, and/or ions that is not crystalline. An amorphous solid does not display a definitive X-ray diffraction pattern.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (ssNMR). For example, the presence of extra peaks in the comparison of an experimentally measured PXRD pattern with a simulated PXRD pattern may indicate more than one crystalline form in the sample. The simulated PXRD may be calculated from single crystal X-ray data. See Smith, D. K., "A FORTRAN Program for Calculating X-Ray Powder Diffraction Patterns", Lawrence Radiation Laboratory, Livermore, Calif., UCRL-7196 (April 1963).

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. Similarly, procedures for converting the crystalline forms, for example, the di-(2-amino-2-(hydroxymethyl)propanediol) ethanolate salt, back to the free acid are known to one skilled in the art.

The forms may be characterized and distinguished using single crystal X-ray diffraction, which is based on unit cell and intensity measurements of a single crystal of a form at a fixed analytical temperature. A detailed description of unit cell and intensity analysis is provided in Stout et al., Chapter 3, *X-Ray Structure Determination: A Practical Guide*, Macmillan Co., New York (1968), which is herein incorporated by reference. Alternatively, the unique arrangement of atoms in spatial relation within the crystalline lattice may be characterized according to the observed fractional atomic coordinates. See Stout et al. reference for experimental determination of fractional coordinates for structural analysis. Another means of characterizing the crystalline structure is by powder X-ray diffraction analysis in which the experimental or observed diffraction profile is compared to a simulated profile representing pure powder material, both at the same analytical temperature, and measurements for the subject form characterized as a series of 2θ values and intensities.

The term "negligible weight loss," as employed herein, as characterized by TGA indicates the presence of a neat (non-solvated) crystal form.

In one embodiment of the invention, a crystalline form of (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate is provided in substantially pure form. This crystalline form may be employed in pharmaceutical compositions which may optionally include one or more other components selected, for example, from the group consisting of excipients, carriers, and one of other active pharmaceutical ingredients or active chemical entities of different molecular structures.

Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

In another embodiment, a composition is provided consisting essentially of the crystalline forms of (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate. The composition of this embodiment may comprise at least 90 weight % of the form, based on its weight in the composition.

The presence of reaction impurities and/or processing impurities may be determined by analytical techniques known in the art, such as, for example, chromatography, nuclear magnetic resonance spectroscopy, mass spectrometry or infrared spectroscopy.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Byrn, S. R. et al., *Solid-State Chemistry of Drugs*, 2nd Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed; for example, the compound may be solubilized into a first solvent to afford a solution, followed by the addition of an antisolvent to decrease the solubility of the compound in the solution and to afford the formation of crystals. An "antisolvent" is a solvent in which the compound has low solubility. Suitable solvents for preparing crystals include polar and nonpolar solvents.

In one method to prepare crystals, (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate is suspended and/or stirred in a suitable solvent to afford a slurry, which may be heated to promote dissolution. The term "slurry," as used herein, means a saturated solution of the free acid, which may also contain an additional amount of the compound to afford a heterogeneous mixture of the compound and a solvent at a given temperature. Suitable solvents in this regard include, for example, polar aprotic solvents and polar protic solvents, and mixtures of two or more of these, as disclosed herein.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in Mullin, J. W. et al., "Programmed cooling of batch crystallizers", *Chemical Engineering Science*, 26:369-377 (1971). In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e., change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, PXRD, or the like, to assure formation of the preferred crystalline form of the product. The resulting crystalline form is typically produced in an amount of greater than about 70 weight % isolated yield, but preferably greater than 90 weight % based on the weight of (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate originally employed in the crystallization procedure. The product may be co-milled or passed through a mesh screen to de-lump the product, if necessary.

Crystalline forms may be prepared directly from the reaction medium of the final process step for preparing (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate. This may be achieved, for example, by employing in the final process step a solvent or mixture of solvents from which the free acid may be crystallized. Alternatively, crystalline forms may be obtained by distillation or solvent addition techniques. Suitable solvents for this purpose include any of those solvents described herein, including protic polar solvents, such as alcohols, and aprotic polar solvents, such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like. By way of general guidance, the reaction solution may be distilled to about 1/10 the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice, as discussed above in connection with solvent exchange. Although the final concentration may vary depending on desired purity, recovery and the like, the final concentration of the free acid in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another through the use of various analytical techniques known to one of ordinary skill in the art. Such techniques include, but are not limited to, X-ray powder diffraction (PXRD). Specifically, the forms may be characterized and distinguished using single crystal x-ray diffraction, which is based on unit cell measurements of a single crystal of a given form at a fixed analytical temperature. A detailed description of unit cells is provided in Stout et al., Chapter 3, *X-Ray Structure Determination: A Practical Guide*, Macmillan Co., New York (1968), which is herein incorporated by reference. Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid state nuclear magnetic resonance (ssNMR) spectroscopy, differential scanning calorimetry (DSC), thermogravimetric analysis (TGA) and gross examination of the crystalline or amorphous morphology. These parameters may also be used in combination to characterize the subject form.

One of ordinary skill in the art will appreciate that an X-ray diffraction pattern may be obtained with a measurement error that is dependent upon the measurement conditions employed. In particular, it is generally known that intensities in an X-ray diffraction pattern may fluctuate depending upon measurement conditions employed and the shape or morphology of the crystal. It should be further understood that relative intensities may also vary depending upon experimental conditions and, accordingly, the exact order of intensity should not be taken into account. Additionally, a measurement error of diffraction angle for a conventional X-ray diffraction pattern is typically about 0.2° or less, preferably about 0.1° (as discussed hereinafter), and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

EXAMPLES

The following Examples further illustrate the present invention, but of course, should not be construed as in any way limiting its scope. Compounds were named using ChemDraw Ultra (CambridgeSoft). The reagents and starting materials are commercially available, or readily synthesized by well-known techniques by one of ordinary skill in the arts.

Example 1

(4'-(2-(1-(2,6-Dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate

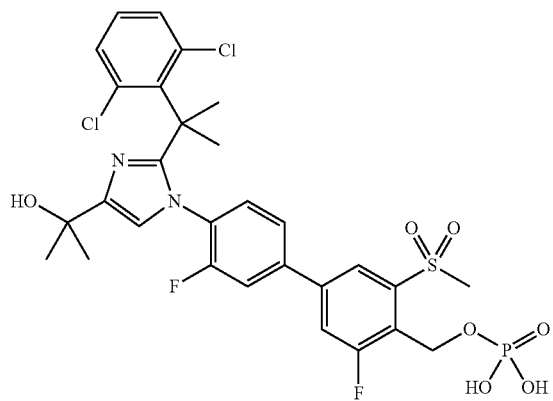 [SMILES: CC(C)(O)c1cn(-c2ccc(-c3cc(F)c(COP(=O)(O)O)c(S(C)(=O)=O)c3)cc2F)c(C(C)(C)c2c(Cl)cccc2Cl)n1]

Step 1. Synthesis of di-tert-butyl (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl phosphate

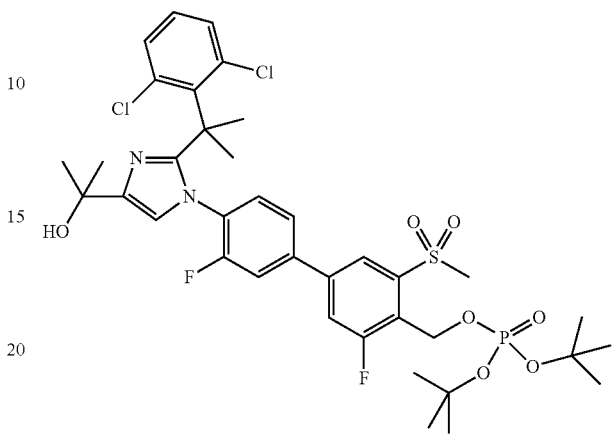

To a solution of 2-(2-(1-(2,6-dichlorophenyl)-1-methylethyl)-1-(3,3'-difluoro-4'-(hydroxymethyl)-5'-(methylsulfonyl)-4-biphenylyl)-1H-imidazol-4-yl)-2-propanol (prepared in the manner described in PCT Publication No. WO 2010/138598, 1.98 g, 3.25 mmol) and di-tert-butyl diisopropylphosphoramidite (1.35 g, 4.87 mmol) in $CH_2CH_2$ (10 mL) was added tetrazole (0.569 g, 8.13 mmol). The resulting suspension was stirred at rt for about 16 hours. After this time, hydrogen peroxide (30%, 8.13 mmol) was added drop-wise and the resulting mixture was stirred for 2 hours. At the conclusion of this period, the reaction mixture was diluted with $CH_2CH_2$ (10 mL), washed with brine, dried and then concentrated to yield the crude product. The crude product was purified by column chromatography (hexane and acetone gradient; 9:1 to 1:1) to afford di-tert-butyl (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl phosphate (0.960 g, 1.20 mmol, 37% yield) as a white solid.

In an alternative method, a hexanes and ethyl acetate (1:1) solvent mixture containing 1.5% of triethylamine was used instead of $CH_2Cl_2$ and the yield of di-tert-butyl (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl phosphate was improved to 47% yield. $^1$H-NMR (300 MHz, $CHCl_3$-d) δ ppm 1.49 (s, 18H), 1.57 (s, 6H), 2.0 (s, 6H), 3.43 (s 3H), 5.5 (s, 2H), 6.59 (s, 1H), 6.88 (m, 1H), 7.01-7.02 (m, 5H), 7.45 (m, 1H), 8.0 (s, 1H); LCMS: (PHENOMENEX® Luna C18, 50 mm×2 mm, 3 μm; Solvent A=5% MeCN: 95% $H_2O$; Solvent B=95% MeCN: 5% $H_2O$; gradient with 1-100% B over 4 min.): retention time=3.66 min; LCMS (APCI), m/z 801.5 (M+1).

Step 2

Example 1

Di-tert-butyl (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl phosphate (5.5 g, 6.9 mmol) was dissolved in toluene (94 mL) and then trifluoroacetic acid (5.18 mL, 10 equiv) was added. The reaction mixture was stirred at rt for 2.5 hours. After this time, analysis by LCMS indicated that the reaction was complete. Acetone (55 mL) and EtOH (5.5 mL) were added, and the resulting mixture was stirred for 2 hours. At the conclusion of this period, the resulting solid was collected by filtration to yield Example 1 (3.5 g) as white crystals. LCMS: (PHENOMENEX® Luna C18, 50×2 mm, 3 μm; Solvent A=5% MeCN: 95% $H_2O$; Solvent B=95% MeCN: 5% $H_2O$; gradient 1-100% B over 4 min.) retention time: 2.10 min; LCMS (APCI), m/z 687.4 (M−1). Example 1 (3.5 g) was further purified using preparatory HPLC (Waters Sunfire prep C18 OBD, 10 μm, 50×300 mm; Solvent A=100% $H_2O$, 10 mmol $NH_4OAc$; Solvent B=90% MeCN, 10% $H_2O$, 10 mmol $NH_4OAc$; gradient 25-50% B over 20 min; 150 mL/min). The product containing fractions were collected and the solvents were removed on a lyophilizer to yield purified Example 1 (2.7 g, 3.9 mmol, 57% yield) as a white solid. The HPLC UV (Waters Acquity BEH C18; 1.7 μm; 150×2.1 mm ID at 35° C.; Solvent A: 30 mM ammonium bicarbonate in $H_2O$ pH 9.5; Solvent B: MeCN; 0.35 mL/min; gradient: hold 10% B for 0-1 min, 10-35% B for 1-25 min, 35-98% B for 25-32 min, hold 98% B for 32-35 min, 98-10% B for 35.0-35.3 min, hold 10% B for 35.3-40 min; UV detection: 260 nm) purity was 99.44%. Using $^1H$-NMR, $NH_4OAc$ was estimated to be approximately one equivalent. $^1H$-NMR (300 MHz, DMSO-$d_6$) δ ppm 7.91 (1H, d, J=1.5 Hz), 7.84-7.90 (1H, m), 7.57 (1H, dd, J=11.3, 1.8 Hz), 7.30 (1H, dd, J=8.2, 1.6 Hz), 7.14 (1H, d, J=1.5 Hz), 7.00-7.13 (3H, m), 6.80 (1H, s), 5.14 (2H, d, J=4.8 Hz), 3.51 (3H, s), 1.94 (6H, s), 1.89 (3H, s), 1.44 (6H, s).

Example 2

(4'-(2-(1-(2,6-Dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate diethyl amine salt

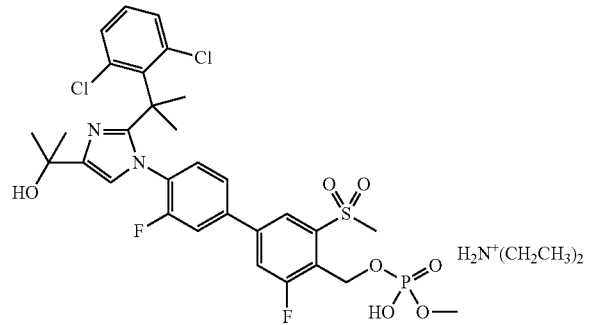

To a solution of the purified Example 1 (5.0 g, 7.2 mmol) in acetone (20 mL) was added dropwise diethyl amine (1.83 mL, 18.1 mmol). The resulting mixture was stirred and hexanes were added. The resulting cloudy suspension was stored at ambient conditions for about 16 hours. After this time, the resulting white precipitate was collected by filtration and dried to yield Example 2 (2.7 g, 3.4 mmol, 47% yield, UV purity: 99.7%) as a white solid. Residual solvent analysis indicated the sample contained diethylamine (10.3% weight/weight), acetone (0.9% weight/weight), and dimethylformamide (0.03% weight/weight). $^1H$ NMR (500 MHz, DMSO-$d_6$) δ ppm 7.92 (1H, d, J=1.9 Hz), 7.89 (1H, dd, J=12.3, 2.0 Hz), 7.59 (1H, dd, J=11.2, 2.0 Hz), 7.31 (1H, dd, J=8.2, 1.9 Hz), 7.14 (2H, d, J=8.51 Hz), 7.12 (1H, d, J=7.88 Hz), 7.04 (1H, dd, J=8.51, 7.25 Hz), 6.81 (1H, s), 5.17 (2H, d, J=5.0 Hz), 3.52 (3H, s), 1.94 (6H, s), 1.44 (6H, s); $^{13}C$ NMR (126 MHz, DMSO-$d_6$) δ ppm 161.81 (d, J=251.2 Hz), 156.86, 153.21, 148.39, 142.06 (d, J=2.9 Hz), 139.62 (d, J=8.6 Hz), 139.34 (d, J=7.7 Hz), 138.57, 134.69, 131.43, 129.96, 128.46, 125.74 (d, J=12.5 Hz), 125.26 (dd, J=16.8, 9.1 Hz), 122.77, 122.50, 118.95 (d, J=25.0 Hz), 116.32, 114.51 (d, J=22.1 Hz), 68.12, 54.91, 44.32, 31.06, 30.55.

Example 3

(4'-(2-(2-(2,6-Dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl) propane-1,3-diol and ethanol (di-(2-amino-2-(hydroxymethyl)propanediol) ethanolate salt)

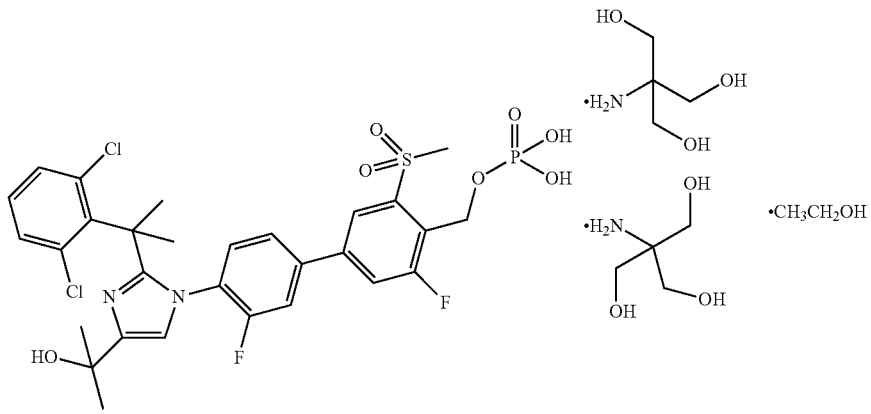

To a reactor was charged 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol (prepared in the manner described in PCT Publication No. WO 2010/138598, 0.50 kg, 804 mmol) followed by acetonitrile (3.9 kg) and the resultant slurry was cooled to −10 to −15° C. Once at the prescribed temperature, diphosphoryl chloride (0.425 kg, 1.65 moles) was added over a period of ~45 min. The resulting mixture was rinsed with acetonitrile and then stirred for one hour. After this time, the reaction was analyzed by HPLC, which indicated the reaction was complete. The reaction mixture was quenched by an inverse addition into a pre-cooled (0 to −5° C.) solution of water (5 kg) and acetonitrile (0.98 kg). Upon completion of addition, the reaction vessel was rinsed with acetonitrile (0.405 kg) and then transferred to the quench vessel. To the quenched reaction mixture was added a potassium phosphate solution (potassium phosphate tribasic, 0.696 kg in water 2.09 kg) such that the temperature was maintained below 20° C. The resulting slurry was filtered, washed with a water:acetonitrile (2 kg:1.57 kg) solution and then acetonitrile (1.5 kg) to afford a wet cake (98.6 area % of Example 1). To a clean separate reactor was added 2-amino-2(hydroxymethyl)-1,3-propanediol (199 g, 1.64 moles) followed by water (2.26 kg). Upon completion of addition, the resulting mixture was stirred at 20° C. until the 2-amino-2(hydroxymethyl)-1,3-propanediol was dissolved. The wet cake was added to the aqueous solution of 2-amino-2(hydroxymethyl)-1,3-propanediol and a mild exotherm to 23° C. was observed. Acetonitrile (3.52 kg) was added resulting in an endotherm to 15° C. After warming the mixture back to 20° C. the solution was polish filtered from the first reactor into a second reactor and the first reactor was rinsed with a solution of water (0.55 kg) and acetonitrile (0.88 kg) to complete the transfer. Additional acetonitrile (4.41 kg) was added to the second reactor over a period of 20 min to effect crystallization of the salt of Example 1 with 2-amino-2-(hydroxymethyl)propane-1,3-diol. The resulting slurry was stirred for ~20 min and then acetonitrile (6.15 kg) was added to the slurry over a two hour period. Upon completion of addition, the resulting slurry was stirred for an additional hour at 20-25° C. After this time, the slurry was filtered and washed with acetonitrile (4.4 kg) to afford a wet cake (99.79 area % of product). This wet cake was added to a clean first reactor containing water (2 kg) at 40° C. and then stirred at 40° C. until a solution was obtained. The resulting solution was polish filtered from this reactor into a second reactor and the first reactor was rinsed with water (0.4 kg) to complete the transfer. Ethanol (12.1 kg) was added to the solution such that the temperature was 40-50° C. The resulting solution was seeded with a slurry of Example 3 (3.8 g, 4.08 mmol) in ethanol (38 mL) which resulted in a thin slurry. The thin slurry was stirred for 15 min and then cooled over a two hour period to 0° C. where it stirred for 30 min. After this time, the slurry was filtered and washed with ethanol (6.02 kg). The resulting wet cake was dried at 20° C. under reduced pressure to constant weight to yield Example 3 as a white solid (0.63 kg, 85% yield, 99.67 area %, 4.28 wt % EtOH and 0.12 wt % water).

Additionally, (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol, Example 3, can be used to prepare (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate, Example 1, as follows:

To a reactor was charged (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (Example 3, 15 g, 15.9 mmol, 98.84 Area %), followed by water (300 mL). The resultant slurry was stirred at 23° C. until dissolution was complete (~60 min). Upon completion of dissolution, the solution was polish filtered through Whatman #1 filter paper into a 500-mL reactor and the filtrate was heated to 60° C. Once at the prescribed temperature, the pH was slowly adjusted to pH 2 (targeting 3) with 1M H$_3$PO$_4$ (35 mL). Once at the prescribed temperature, the mixture was heated to 60° C., where it stirred for 1 h. After this time, the mixture was cooled to 20° C. during a 2 h period. Once at the prescribed temperature, the mixture was stirred for at least 1 h. After this time, the resulting slurry was filtered and the wet cake was washed with water (120 mL). The wet cake was dried at 60° C./25 in Hg over night to afford Example 1 (10.66 g, 97% yield, 98.88 Area %).

Example 4

(4-Phosphonooxy-phenyl)acetic acid 4'-[2-[1-(2,6-dichloro-phenyl)-1-methyl-ethyl]-4-(1-hydroxy-1-methyl-ethyl)-imidazol-1-yl]-3,3'-difluoro-5-methanesulfonyl-biphenyl-4-ylmethyl ester

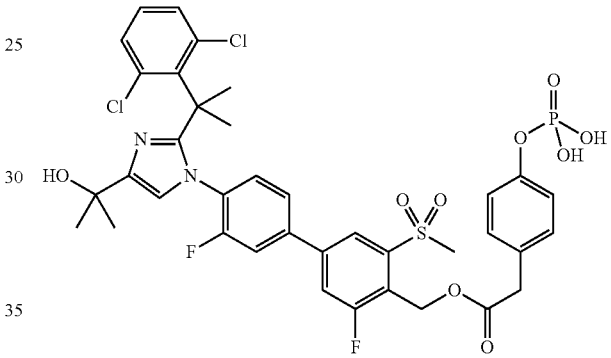

Step 1. Synthesis of methyl 2-(4-(bis(benzyloxy)phosphoryloxy)phenyl)acetate

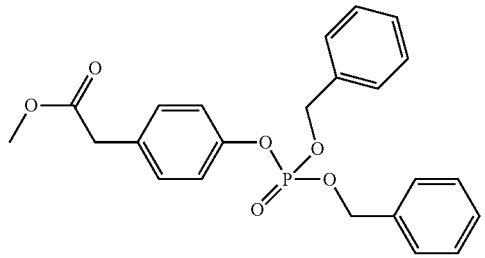 [SMILES: COC(=O)Cc1ccc(OP(=O)(OCc2ccccc2)OCc2ccccc2)cc1]

To a solution of methyl 2-(4-hydroxyphenyl)acetate (5 g, 30 mmol) in CH$_2$Cl$_2$ (25 mL) at 25° C. under nitrogen was added dibenzyl diisopropylphosphoramidite (20.8 g, 60.2 mmol) followed by 1H-tetrazole (0.45 mol solution in acetonitrile). The mixture contained some solids that dissolved after several minutes. The reaction appeared complete after 3 h by TLC monitoring. The reaction flask was cooled to 0° C. and H$_2$O$_2$ (2 mL) was added dropwise over 5 min. The reaction appeared complete after 1 h by TLC, and then the mixture was diluted with EtOAc (150 mL), and washed with brine (2×20 mL). The organic layer was dried over sodium sulfate and concentrated to give crude product, which was purified by column chromatography using a mixture of EtOAc and hexanes (1:3) to afford 10 g (23 mmol, 78% yield) of methyl 2-(-4-bis(benzyloxy)phosphoryloxy)phenyl)acetate. LCMS: (CHROMOLITH® SpeedROD C18, 30×4.6 mm, 5 µm; Solvent A=10% MeOH: 90% H$_2$O: 0.1% TFA; Solvent B=90% MeOH: 10% H$_2$O: 0.1% TFA; gradient 0-100% B over 2 min) retention time: 2.03 min; LCMS (ES-API), m/z 427.0 (M+H).

Step 2: 2-(4-(Bis(bezyloxy)phosphoryloxy)phenyl) acetic acid

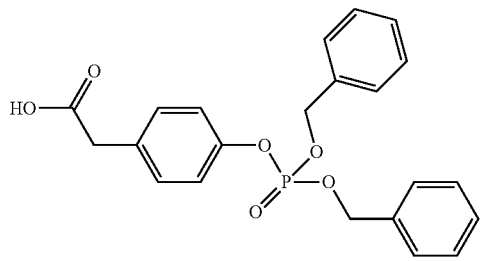 [SMILES: O=C(O)Cc1ccc(OP(=O)(OCc2ccccc2)OCc2ccccc2)cc1]

To a solution of methyl 2-(-4-bis(benzyloxy)phosphoryloxy)phenyl) acetate (10 g, 23 mmol) in THF (100 mL) and methanol (30 mL) was added a solution of lithium hydroxide (1.45 g, 35.2 mmol) in water (35 mL) at 0° C. The reaction mixture was stirred at 0° C. for 4 h. While the reaction vessel was in an ice bath, the reaction mixture was acidified to pH=2 by addition of 1.5 N HCl. The organic solvents were removed under reduced pressure. Ethyl acetate (3×200 mL) was added to the vessel, and the mixture was transferred to a separatory funnel. The organic layer was separated, dried over sodium sulfate and concentrated under reduced pressure to provide the crude product, which was purified by column chromatography using a mixture of CHCl$_3$: MeOH (9:1) to afford 7.0 g (17 mmol, 72%) of 2-(4-(bis(benzyloxy)phosphoryloxy)phenyl) acetic acid. $^1$H NMR (400 MHz, DMSO-d$_6$) δ 3.57 (s, 2H), 5.15 (d, J=8.4, 4H), 7.11 (d, J=8.4, 2H), 7.26 (d, J=8.4, 2H), 7.35-7.40 (m, 10H), 12.37 (s, 1H). LCMS m/z=413.

Step 3: Synthesis of (4'-(2-(2-(2,6-dichlorophenyl) propan-2-yl)-4-(2-hydroxypropan-2-yl)-1H-imidazol-1-yl)-3,3'-difluoro-5-(methylsulfonyl)biphenyl-4-yl)methyl 2-(4-(bis(benzyloxy)phosphoryloxy) phenyl)acetate

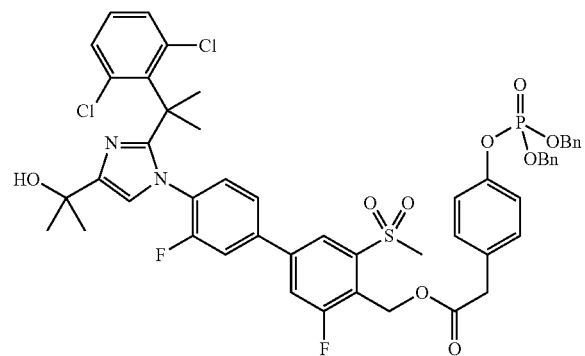 [SMILES: CC(C)(O)c1cn(-c2ccc(-c3cc(F)c(COC(=O)Cc4ccc(OP(=O)(OCc5ccccc5)OCc5ccccc5)cc4)c(S(C)(=O)=O)c3)cc2F)c(C(C)(C)c2c(Cl)cccc2Cl)n1]

4-Dimethylaminopyridine (0.19 g, 1.6 mmol) was added to a solution of 2-(4-(bis(benzyloxy)phosphoryloxy)phenyl) acetic acid (0.67 g, 1.6 mmol), 2-(2-(2-(2,6-dichlorophenyl) propan-2-yl)-1-(3,3'-difluoro-4'-(hydroxymethyl)-5'-(methylsulfonyl)biphenyl-4-yl)-1H-imidazol-4-yl)propan-2-ol (prepared in the manner described in PCT Publication No. WO 2010/138598, 0.4 g, 0.6 mmol), and N,N'-dicyclohexylcarbodiimide (0.37 g, 1.8 mmol) in CH$_2$Cl$_2$ (5 mL). The mixture was stirred at rt for 30 mins. After this time, the reaction mixture was filtered, and the organic solvents were removed under reduced pressure to yield the crude product. The crude product was purified by column chromatography using a mixture of CHCl$_3$ and methanol (9:1) to afford (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl 2-(4-(bis(benzyloxy)phosphoryloxy) phenyl)acetate (0.4 g, 0.4 mmol, 60% yield). $^1$H NMR (400 MHz, CHCl$_3$-d) δ 1.60 (s, 6H), 2.03 (s, 6H), 2.99 (s, 3H), 3.65 (s, 2H), 5.11 (d, J=8.4, 2H), 5.67 (s, 2H), 6.62 (s, 1H), 6.88 (t, J=7.6, 1H), 6.8-7.98 (m, 22H), 7.98 (s, 1H). LCMS: (Ascentis Express C18, 5×2.1 mm, 2.7 µm; Solvent A=2% MeCN: 98% H$_2$O: 10 mM NH$_4$COOH; Solvent B=98% MeCN: 2% H$_2$O: 10 mM NH$_4$COOH; gradient 0-100% B over 1.5 min) retention time: 2.38 min; LCMS (ES-API), m/z 1005.2 (M+H).

Step 4

Example 4

To a solution of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl 2-(4-(bis (benzyloxy)phosphoryloxy)phenyl)acetate (0.4 g, 0.39 mmol) in methanol (20 mL) was added Pd/C (40 mg, 10% w/w) under an atmosphere of hydrogen at rt for 15 min. The reaction mixture was filtered and the solvents were removed under reduced pressure to afford crude product. The crude product was purified by preparatory HPLC to afford Example 4. $^1$H NMR (400 MHz, DMSO-d$_6$) δ 1.45 (s, 6H), 1.96 (s, 6H), 3.31 (s, 3H), 3.63 (s, 2H), 4.73 (br s, 1H), 5.53 (s, 2H), 6.83 (s, 1H), 7.03-7.20 (m, 8H), 7.38 (d, J=8, 1H), 7.67 (d, J=11.2, 1H), 7.98 (d, J=9.2, 2H). LCMS: (Atlantis C18, 50×4.6 mm, 5 µm; Solvent A=10 mM NH$_4$OAc; Solvent B=MeCN; gradient 30-95% B over 3 min.) retention time: 2.17 min; LCMS (ES-API), m/z 823.2 (M+H).

Example 5

Phosphoric acid mono-{4'-[2-[1-(2,6-dichloro-phenyl)-1-methyl-ethyl]-4-(1-hydroxy-1-methyl-ethyl)-imidazol-1-yl]-3,3'-difluoro-5-methanesulfonyl-biphenyl-4-ylmethoxymethyl}ester

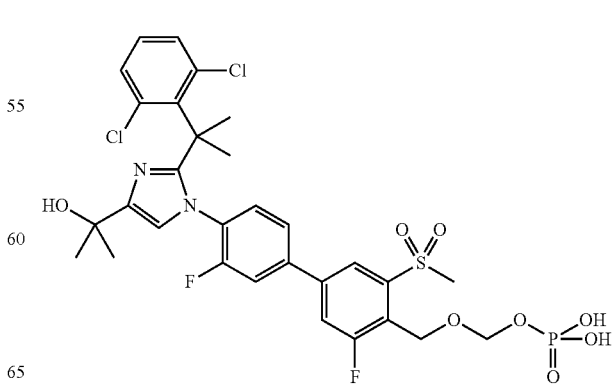

Step 1: Synthesis of di-tert-butyl ((4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methoxy)methyl phosphate

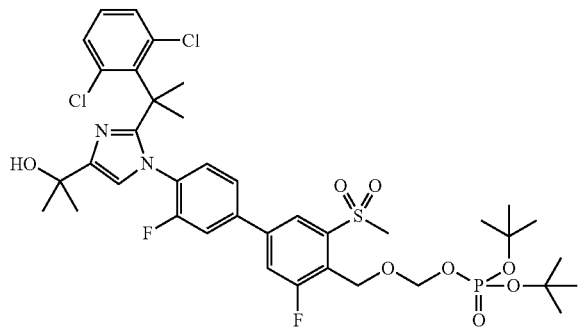 [SMILES: CC(C)(C)OP(=O)(OCOCc1c(F)cc(-c2ccc(-n3cc(C(C)(C)O)nc3C(C)(C)c3c(Cl)cccc3Cl)c(F)c2)cc1S(C)(=O)=O)OC(C)(C)C]

To a stirred solution of 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol (prepared in the manner described in PCT Publication No. WO 2010/138598, 100 mg, 0.164 mmol) in 2 mL of dimethoxyethane was added NaH (60%, 11.8 mg, 0.328 mmol) at −60° C. After the reaction mixture was stirred for 10 min at −60° C., chloromethylditertiarybutylphosphate (62 mg, 0.25 mmol) and sodium iodide (36.6 mg, 0.246 mmol) were added. The temperature was maintained at −60° C. for 2 hours, and then the reaction vessel was warmed to rt. The reaction mixture was stirred for 2 hours at rt and then poured into cold water (10 mL). Ethyl acetate (3×15 mL) was added, and the organic phase was separated, dried over anhydrous sodium sulfate, filtered and concentrated under vacuum to afford 150 mg of crude product (42% by LCMS). The crude product was precipitated from a mixture of diethyl ether (2 mL) and hexanes (8 mL) to give 70 mg of di-tert-butyl ((4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methoxy)methyl phosphate with 80% purity by LCMS. LCMS: (Atlantis dC18 (50×4.6 mm-5 μm); Solvent A=10 mM NH₄OAc in H₂O; Solvent B=acetonitrile; gradient 40-95% (3 min), 95% (3-6 min), 95-40% (6-6.5 min), 40% (6.5-8 min) B.) retention time: 3.095 min; LCMS (MM-ES+ APCI), flow 1.5 ml/min, m/z=831.

Step 2

Example 5

A stirred solution of di-tert-butyl ((4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methoxy)methyl phosphate (50 mg, 0.06 mmol) in acetone:water (1:1, 4 mL) was heated to 60° C. for 16 h. The solvents were removed and the crude product was purified by preparatory HPLC to afford Example 5 (17 mg, 0.024 mmol, 40% yield). $^1$H NMR (400 MHz, DMSO-$d_6$) δ 7.96 (s, 2H), 7.94 (s, 1H), 7.64 (d, J=12.8, 2H), 7.35 (d, J=8, 2H), 7.11-7.15 (m, 4H), 7.04 (t, J=7.2, 2 H), 6.82 (1H), 5.04 (s, 2H), 4.97 (d, J=9.2, 2H), 4.56 (brs, 1H), 3.43 (s, 3H), 1.95 (s, 6H), 1.45 (s, 6H). LCMS m/z=720.

Example 6

(E)-4-((4'-(2-(2-(2,6-Dichlorophenyl)propan-2-yl)-4-(2-hydroxypropan-2-yl)-1H-imidazol-1-yl)-3,3'-difluoro-5-(methylsulfonyl)biphenyl-4-yl)methoxy)-4-oxobut-2-enoic acid

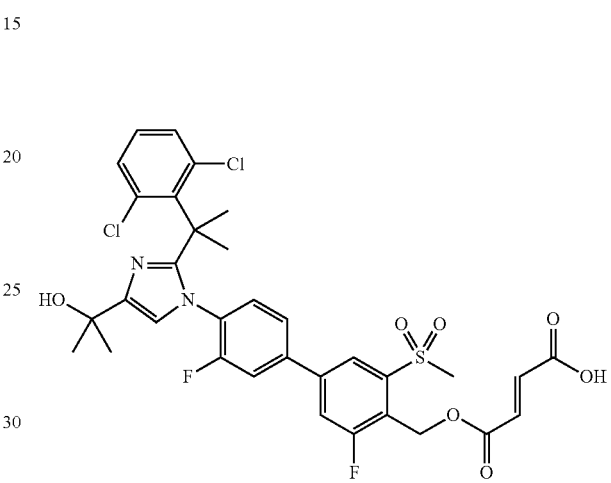

Step 1: Synthesis of tert-butyl (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl fumarate

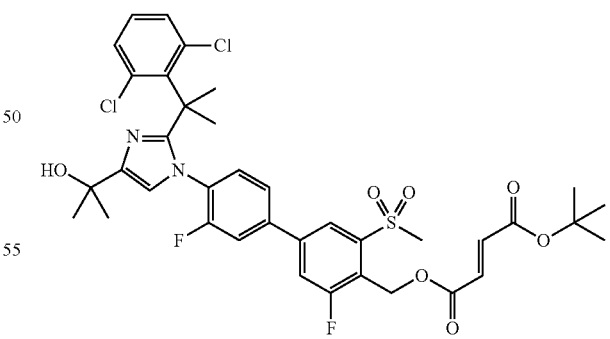

To a stirred solution of 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol (prepared in the manner described in PCT Publication No. WO 2010/138598, 100 mg, 0.16 mmol) in CH₂Cl₂ (2 mL) was added N,N'-di-tert-butylcarbodiimide hydrochloride (47 mg, 0.24 mmol), 4-(dimethylamino)pyridine (10 mg, 0.08 mmol)

and mono-tert-butylfumerate ester (42 mg, 0.24 mmol) at rt. The reaction mixture was stirred at rt overnight. The mixture was diluted with CH$_2$Cl$_2$ (10 mL) and was washed with water (3×3 mL). The organic layer was dried over anhydrous sodium sulfate and concentrated to afford 150 mg of the crude product with 77% LCMS purity. The crude product was purified by silica gel column chromatography, and the product eluted off the column at 40% EtOAc in Hexanes to afford 100 mg (80%, 0.13 mmol) of tert-butyl (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl) methyl fumarate with 96% LCMS purity. LCMS: (Ascentis Express C18 (50×2.1 mm-2.7 µm); Solvent A=10 mM NH$_4$COOH in 98% H$_2$O and 2% acetonitrile; Solvent B=98% acetonitrile and 2% 10 mM NH$_4$COOH in H$_2$O; gradient 0-100% (1.5 min) then 100% (1.5-3.2 min), 100-0% (3.2-3.6 min), 0% (3.6-4 min) B over 4 min.) retention time: 2.345 min; LCMS (MM-ES+APCI), flow 1 ml/min, m/z: 763.

Step 2

Example 6

To a stirred solution of tert-butyl (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl) methyl fumarate (0.10 g, 0.13 mmol) in CH$_2$Cl$_2$ (2 mL) was added TFA (10% in CH$_2$Cl$_2$, 2 mL) drop-wise over a period of 10 min at 0° C. The mixture was warmed to rt, and stirred for 4 hrs. Then the solvents were removed under vacuum to obtain 90 mg of crude product with 70% purity. The crude product was purified by preparative HPLC to afford Example 6 (40 mg, 0.056 mmol, 43% yield). $^1$H NMR (400 MHz, DMSO-d$_6$) δ 7.99 (d, J=6.8, 2H), 7.68 (dd, J=1.6 and 11.2, 1H), 7.39 (dd, J=1.6 and 10, 1H), 7.12-7.15 (m, 3H), 7.05 (dd, J=6.8 and 8.4, 1H), 6.83 (s, 1H), 6.75 (d, J=16, 1H), 6.45 (d, J=16, 1H), 5.61 (s, 2H), 4.70 (s, 1H), 3.42 (s, 3H), 1.95 (s, 6H), 1.91 (s, 1H) 1.45 (s, 6H). LCMS m/z: 707.

Example 7

Succinic acid mono-{4'-[2-[1-(2,6-dichloro-phenyl)-1-methyl-ethyl]-4-(1-hydroxy-1-methyl-ethyl)-imidazol-1-yl]-3,3'-difluoro-5-methanesulfonyl-biphenyl-4-ylmethyl} ester

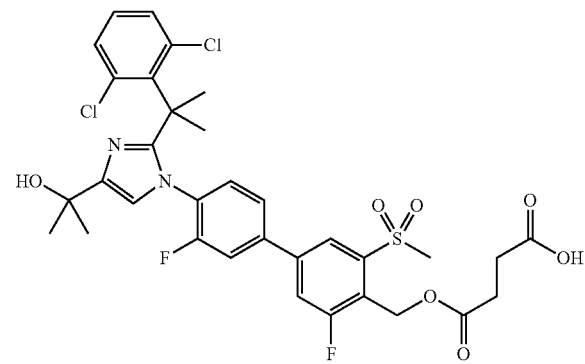 [SMILES: CC(C)(O)c1cn(-c2ccc(-c3cc(F)c(COC(=O)CCC(=O)O)c(S(C)(=O)=O)c3)cc2F)c(C(C)(C)c2c(Cl)cccc2Cl)n1]

To a stirred solution of 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol (prepared in the manner described in PCT Publication No. WO 2010/138598, 50 mg, 0.082 mmol) in pyridine (1 mL) was added 4-(dimethylamino)pyridine (5 mg, 0.04 mmol) and succinic anhydride (9.8 mg, 0.098 mmol) at rt. The reaction mixture was stirred at rt overnight. The solvents were removed under reduced pressure, and the crude product was purified by preparative HPLC to afford Example 7 (35 mg, 0.049 mmol, 60% yield). $^1$H NMR (400 MHz, DMSO-d$_6$) δ 7.97-7.99 (m, 2H), 7.69 (dd, J=1.6 and 11.2, 1H), 7.39 (d, J=8.0, 1H), 7.13-7.17 (m, 3H), 7.04 (dd, J=7.6 and 8.8, 1H), 6.83 (s, 1H), 5.52 (s, 2H), 4.70 (s, 1H), 3.41 (s, 3H), 2.46-2.54 (m, 4H), 1.95 (s, 6H), 1.45 (s, 6H). LCMS m/z: 709.2.

Example 8

(4'-(2-(2-(2,6-Dichlorophenyl)propan-2-yl)-4-(2-hydroxypropan-2-yl)-1H-imidazol-1-yl)-3,3'-difluoro-5-(methylsulfonyl)biphenyl-4-yl)methyl 3-(phosphonooxymethyl)benzoate

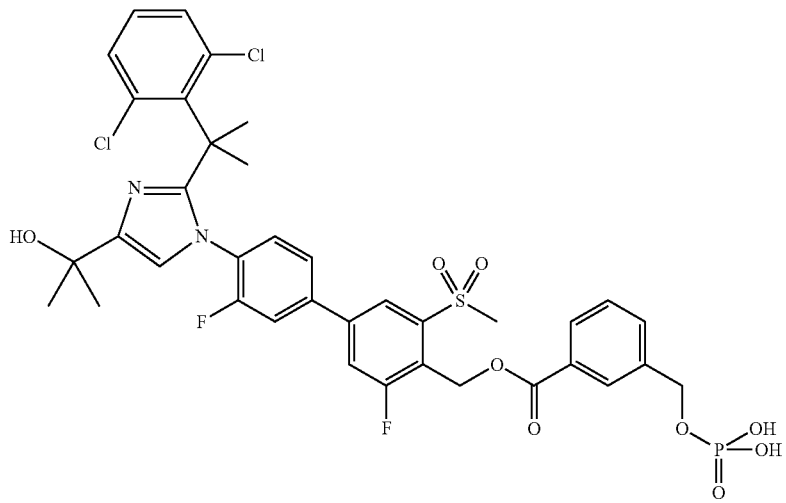 [SMILES: CC(C)(O)c1cn(-c2ccc(-c3cc(F)c(COC(=O)c4cccc(COP(=O)(O)O)c4)c(S(C)(=O)=O)c3)cc2F)c(C(C)(C)c2c(Cl)cccc2Cl)n1]

Step 1: Synthesis of methyl 3-((di-tert-butoxyphosphoryloxy)methyl)benzoate

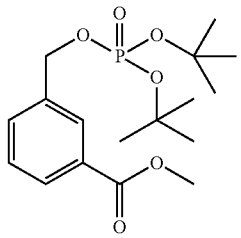 [SMILES: COC(=O)c1cccc(COP(=O)(OC(C)(C)C)OC(C)(C)C)c1]

To a stirred solution of methyl-3-(bromomethyl)benzoate (0.5 g, 2 mmol) in THF (10 mL) was added potassium ditertiary butyl phosphate (0.5 g, 2 mmol). The reaction flask was heated to 70° C. for 2 h. After the flask was cooled to rt, EtOAc (50 mL) was added to the mixture. The organics were washed with brine (2×10 mL), dried over anhydrous sodium sulfate, and evaporated under vacuum to yield methyl 3-((di-tert-butoxyphosphoryloxy)methyl)benzoate (0.35 g, 0.9 mmol). $^1$H NMR (400 MHz, CHCl$_3$-d): δ 1.47 (s, 18H), 3.91 (s, 3H), 5.03 (d, 2H, J=7.6 Hz), 7.44 (t, J=7.6 1H), 7.60 (dd, J=1.2 and 7.2), 7.98 (ddd, J=1.2, 2.8 and 7.6, 1H), 8.05 (t, J=0.4, 1H).

Step 2: Synthesis of 3-((di-tert-butoxyphosphoryloxy)methyl)benzoic acid

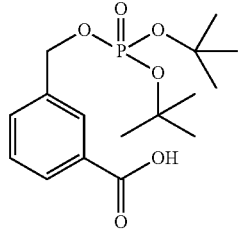 [SMILES: CC(C)(C)OP(=O)(OCc1cccc(C(=O)O)c1)OC(C)(C)C]

To a solution of methyl 3-((di-tert-butoxyphosphoryloxy)methyl)benzoate (0.1 g, 0.3 mmol) in THF (3 mL), methanol (3 mL), water (3 mL) was added lithium hydroxide (0.035 g, 0.81 mmol). The reaction mixture was stirred at rt for 1 h. After this time, the organic solvents were removed under reduced pressure, and EtOAc (30 mL) was added to the residual material followed by acetic acid (30%). The organic layer was washed with water (2×10 mL), dried over Na$_2$SO$_4$ and concentrated under vacuum to afford 3-((di-tert-butoxyphosphoryloxy)methyl)benzoic acid (80 mg, 0.23 mmol). $^1$H NMR (400 MHz, DMSO-d$_6$): 1.41 (s, 18H), 5.00 (d, J=8, 2H), 7.52 (t, J=7.6, 1H), 7.62 (d, J=7.6, 1H), 7.90 (d, J=8.0, 1H), 7.99 (s, 1H). LCMS-m/z: 343.2.

Step 3: Synthesis of (4'-(2-(2-(2,6-dichlorophenyl)propan-2-yl)-4-(2-hydroxypropan-2-yl)-1H-imidazol-1-yl)-3,3'-difluorobiphenyl-4-yl)methyl 3-((di-tert-butoxyphosphoryloxy)methyl)benzoate

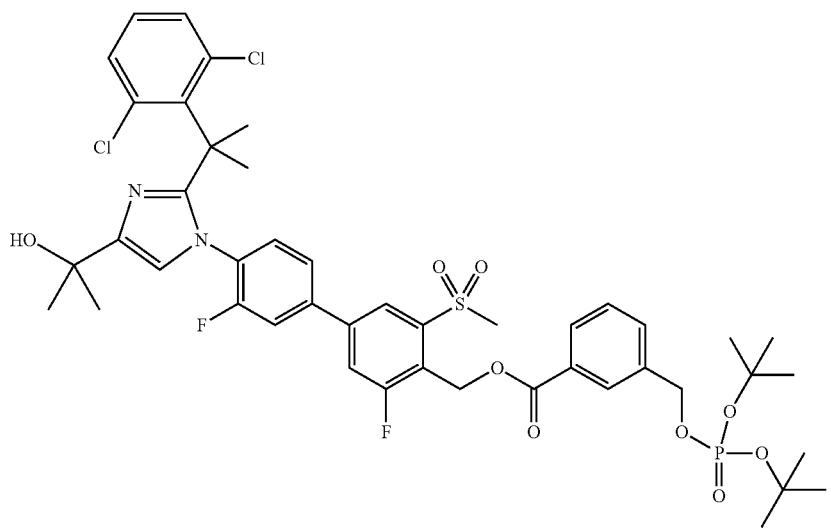 [SMILES: CC(C)(C)OP(=O)(OCc1cccc(C(=O)OCc2c(F)cc(-c3ccc(-n4cc(C(C)(C)O)nc4C(C)(C)c4c(Cl)cccc4Cl)c(F)c3)cc2S(C)(=O)=O)c1)OC(C)(C)C]

To a stirred solution of 2-(2-(2-(2,6-dichlorophenyl)propan-2-yl)-1-(3,3'-difluoro-4'-(hydroxymethyl)-5'-(methylsulfonyl)biphenyl-4-yl)-1H-imidazol-4-yl)propan-2-ol (prepared in the manner described in PCT Publication No. WO 2010/138598, 0.1 g, 0.16 mmol) in $CH_2Cl_2$ (2 mL) was added 3-((di-tert-butoxyphosphoryloxy)methyl)benzoic acid (140 mg, 0.40 mmol), DMAP (4 mg, 0.33 mmol) and DCC (86 mg, 0.42 mmol). The reaction mixture was stirred at rt. After 15 h, the reaction mixture was filtered, washed with $CH_2Cl_2$ (2×10 mL), and the solvents were removed under reduced pressure to yield the crude material. The crude product was purified by column chromatography (basic alumina, EtOAc:Hexane) to afford (4'-(2-(2-(2,6-dichlorophenyl)propan-2-yl)-4-(2-hydroxypropan-2-yl)-1H-imidazol-1-yl)-3,3'-difluorobiphenyl-4-yl)methyl 3-((di-tert-butoxyphosphoryloxy)methyl)benzoate (95 mg, 0.10 mmol, 62%). LCMS: (Ascentis Express C8 (50×2.1 mm-2.7 μm); Solvent A=10 mM $NH_4COOH$ in 98% $H_2O$ and 2% acetonitrile; Solvent B=98% acetonitrile and 2% 10 mM $NH_4COOH$ in $H_2O$; gradient 0% (1.5 min) then to 100% (1.5-3.2 min), 100% (3.2-4 min) B over 4 min), retention time: 2.22 min; LCMS (MM-ES+ APCI), flow 1 mL/min, m/z 937.2.

Step 4

Example 8

To a stirred solution of (4'-(2-(2-(2,6-dichlorophenyl)propan-2-yl)-4-(2-hydroxypropan-2-yl)-1H-imidazol-1-yl)-3,3'-difluorobiphenyl-4-yl)methyl 3-((di-tert-butoxyphosphoryloxy)methyl)benzoate (100 mg, 0.11 mmol) in $CH_2Cl_2$ (10 mL) was added TFA (10% in $CH_2Cl_2$, 4 mL) drop-wise over a period of 10 min at 0° C. The reaction vessel was warmed to rt, and the reaction mixture was stirred for 4 hrs. After this time, the solvents were removed under reduced pressure to yield the crude product. The crude product was purified by preparative HPLC to afford Example 8 (35 mg, 0.042 mmol, 38% yield). $^1$H NMR (400 MHz, DMSO-$d_6$): 1.51 (s, 6H), 2.01 (s, 6H), 3.46 (s, 3H), 4.96 (d, 2H, J=8 Hz), 5.80 (s, 2H), 7.11-7.23 (m, 4H), 7.34 (brs, 1H), 7.514-7.563 (m, 2H), 7.68 (d, J=7.6, 1H), 7.79 (d, J=10.8, 1H), 7.90 (d, J=7.6, 1H), 7.97 (s, 1H), 8.05 (t, J=4.4, 2H). LCMS: m/z: 822.9.

Crystal forms of (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate, free acid were characterized as described below.

Procedures for Characterizing the Forms

Single Crystal Data

Single crystal X-ray diffraction data were collected on a Bruker-Nonius Kappa CCD 2000 system using CuKα radiation (λ=1.5418 Å). Indexing and processing of the measured intensity data were carried out with the HKL2000 software package[1] in the Collect program suite.[2] Alternately, single crystal data were collected on a Bruker-AXS APEX2 CCD system using CuKα radiation (λ=1.5418 Å). Indexing and processing of the measured intensity data were carried out with the Bruker-AXS APEX2/SAINT software package/program suite[3].

[1] Otwinowski, Z. et al., *Macromolecular Crystallography*, 276:307-326 Carter, W. C., Jr. et al., eds., Academic, NY (1997).
[2] Collect Data collection and processing user interface: Collect Data collection software, R. W. W. Hooft, Bruker AXS B.V., P.O. Box 811, 2600 AV Delft, The Netherlands (1998).
[3] APEX2 Data collection and processing user interface: APEX2 User Manual, Vol. 27; Bruker AXS, Inc., 5465 East Cheryl Parkway Madison, Wis. 53711 USA When indicated, crystals were cooled in the cold stream of an Oxford cryo-system[4] during data collection.

[4] Oxford Cryosystems Cryostream cooler: Cosier, J. et al., *J. Appl. Cryst.*, 19:105 (1986).

The structures were solved by direct methods and refined on the basis of observed reflections using either the crystallographic software packages maXus[5] or SHELXTL[6].

[5] Mackay S., et al., "maXus Computer Program for the Solution and Refinement of Crystal Structures" 1999. Bruker Nonius, The Netherlands; MacScience, Japan & The University of Glasgow.
[6] Sheldrick G. M., *Acta Cryst.* A, 64 112-122 (2008).

The derived atomic parameters (coordinates and temperature factors) were refined through full matrix least-squares. The function minimized in the refinements was $\Sigma_w(|F_O|-|F_C|)^2$. R is defined as $\Sigma||F_O|-|F_C||/\Sigma|F_O|$ while $R_w = [\Sigma_w(|F_O|-|F_C|)^2/\Sigma_w|F_O|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

X-ray Powder Diffraction Data (PXRD)

X-ray powder diffraction (PXRD) data were obtained using a Bruker C2 GADDS. The radiation was CuKα (40 KV, 40 mA). The sample-detector distance was 15 cm. Powder samples were placed in sealed glass capillaries of 1 mm or less in diameter; the capillary was rotated during data collection. Data were collected for 3≤2θ≤35° with a sample exposure time of at least 1000 seconds. The resulting two-dimensional diffraction arcs were integrated to create a traditional 1-dimensional PXRD pattern with a step size of 0.02 degrees 2θ in the range of 3 to 35 degrees 2θ.

Differential Scanning Calorimetry (DSC)

Differential scanning calorimetry (DSC) experiments were performed in a TA INSTRUMENTS® model Q2000, Q1000 or 2920. The sample (about 2-6 mg) was weighed in an aluminum pan and recorded accurately to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

Thermal Gravimetric Analysis (TGA)

Thermal gravimetric analysis (TGA) experiments were performed in a TA INSTRUMENTS® model Q 5000, Q500 or 2950. The sample (about 3-30 mg) was placed in a platinum pan previously tared. The weight of the sample was measured accurately and recorded to a thousand of a milligram by the instrument. The furnace was purged with nitrogen gas at 100 mL/min. Data were collected between room temperature and 300° C. at 10° C./min heating rate.

$^{13}$C Solid-State Nuclear Magnetic Resonance ($^{13}$C ssNMR)

All solid-state C-13 NMR measurements were made with a Bruker AVIII-400 MHz NMR spectrometer. High resolution spectra were obtained using a ramped cross-polarization (RAMP-CP) sequence with TPPM proton decoupling during acquisition. (Bennett, A. E. et al., *J. Chem. Phys.*, 103:6951 (1995)), (Metz, G. et al., *J. Magn. Reson. A*, 110:219-227 (1994)). Approximately 70 mg of sample, packed into a 4 mm canister-design zirconia rotor, was used for each experiment. Chemical shifts (δ) were referenced to external adamantane with the high frequency resonance being set to 38.56 ppm (Earl, W. L. et al., *J. Magn. Reson.*, 48:35-54 (1982)).

$^{19}$F Solid-State Nuclear Magnetic Resonance ($^{19}$F ssNMR)

All solid-state F-19 NMR measurements were made Bruker AVIII-400 MHz NMR spectrometer using a 4 mm CFH triple resonance probe. The data were acquired using a single pulse experiment with a spinning speed of 16 KHz. Approximately 70 mg of sample, packed into a 4 mm canister-design zirconia rotor, was used for each experiment. Chemical shifts were referenced to external PTFE (−123.3 ppm).

Analysis of the Forms

The unit cell data and other properties for Form H-1 of the present invention are presented in Table 1. The unit cell parameters were obtained from single crystal X-ray crystallographic analysis. A detailed account of unit cells can be found in Chapter 3 of Stout et al., *X-Ray Structure Determination: a Practical Guide*, Macmillan (1968).

Fractional atomic coordinates for Form H-1 and the conditions at which they were measured are presented in Table 2.

Additionally, characteristic powder x-ray diffraction peak positions (degrees 2θ±0.1) at RT for Forms E-1 and H-1 presented in Table 3, all of which are based on high quality patterns collected with a diffractometer (CuKα) with a spinning capillary with 2θ calibrated with a NIST or other suitable standard.

Form H-1, (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate. Form H-1 free acid was characterized by an experimental PXRD pattern which matches the simulated pattern generated from the single crystal structure data.

The characteristic resonance peaks for the solid state carbon spectrum of Forms E-1 and H-1 are listed below in Table 4. Crystal structures demonstrating substantially similar $^{13}$C ssNMR peak positions, wherein "substantially similar" means 10 to 15% of dimensionless value, are deemed to fall within the scope of the invention (i.e., equivalent to the E-1 and H-1 Forms illustrated below).

Figure 3:
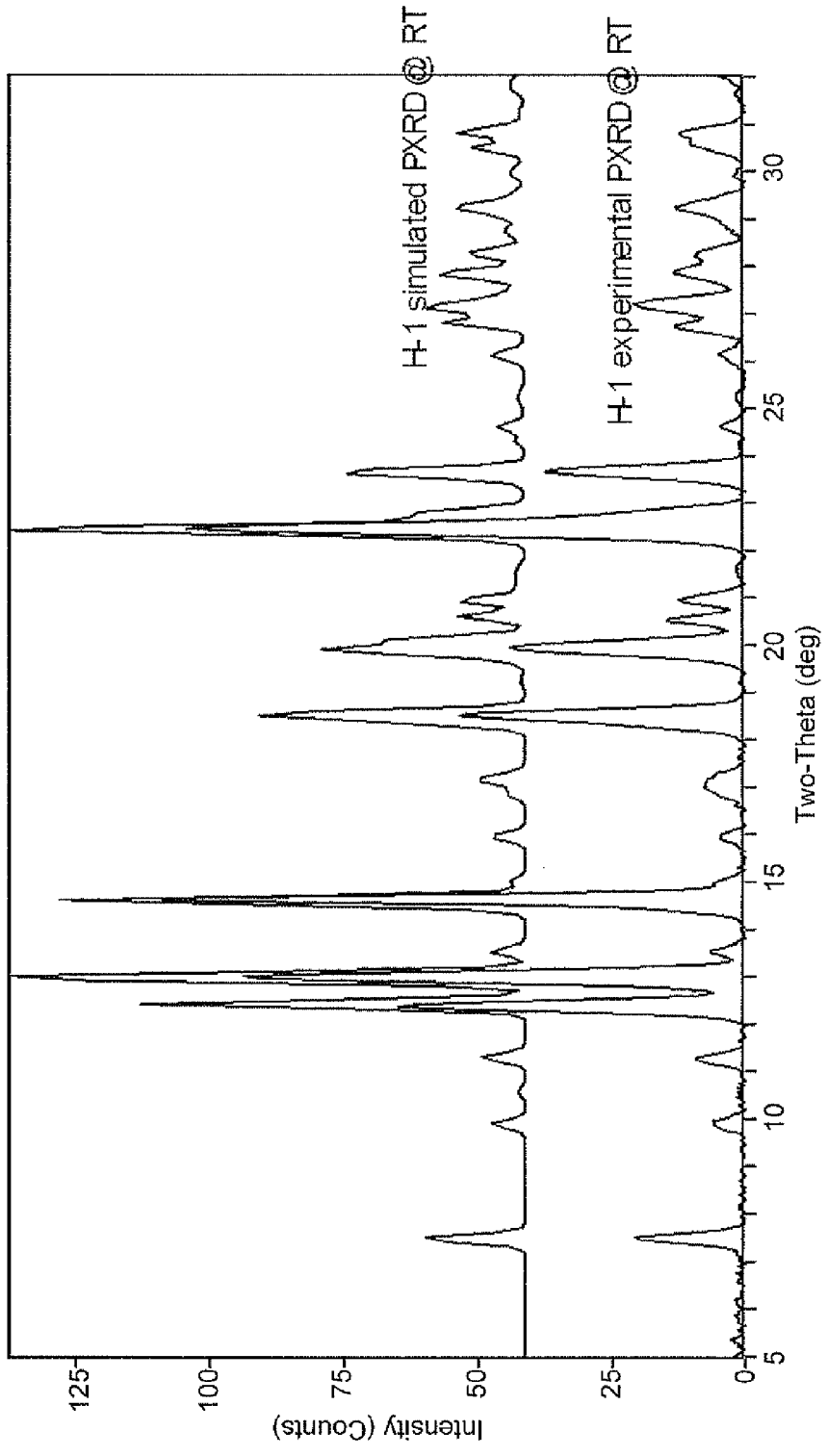
FIG. 3. Experimental and simulated powder X-ray diffraction patterns of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate, Form H-1.
Figure 4:
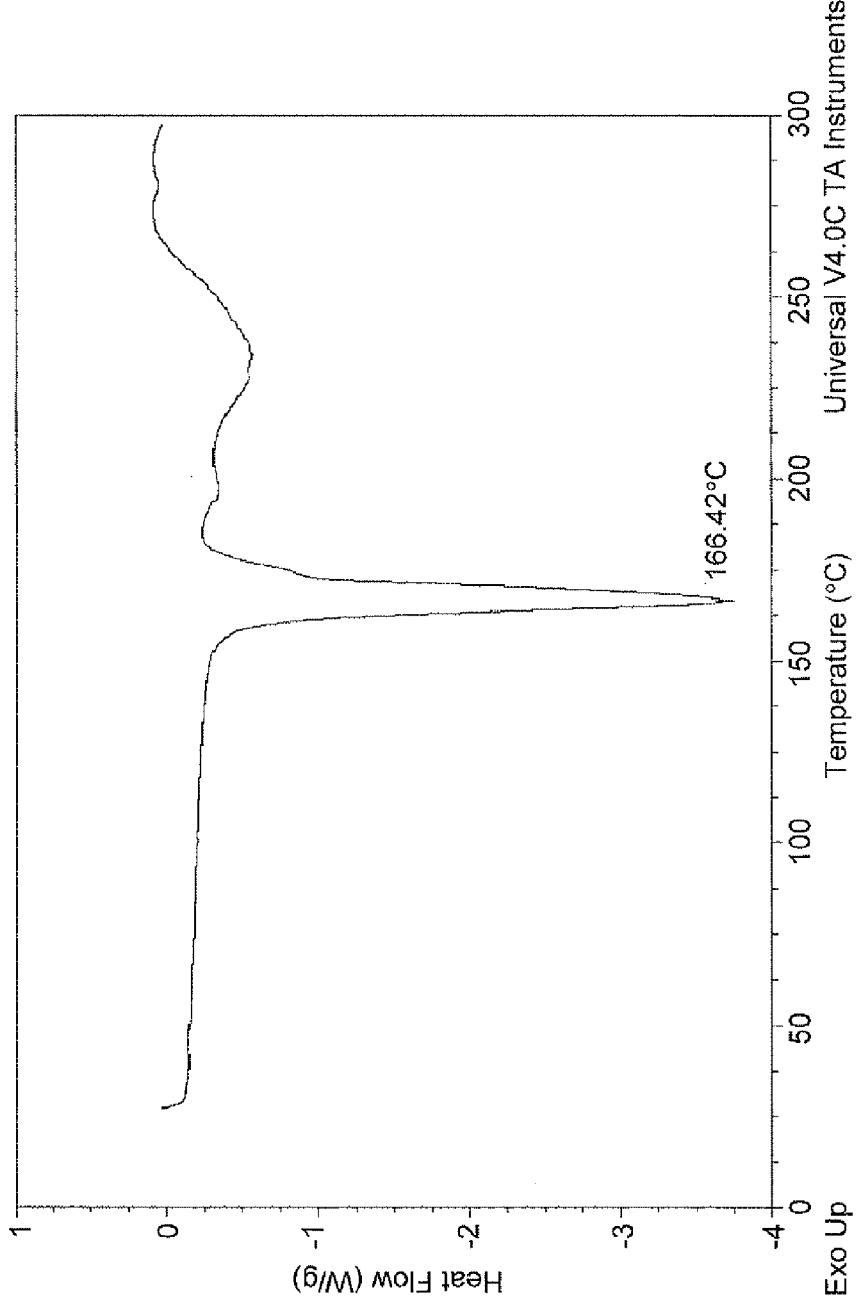
FIG. 4. DSC of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt), Form E-1.
Figure 5:
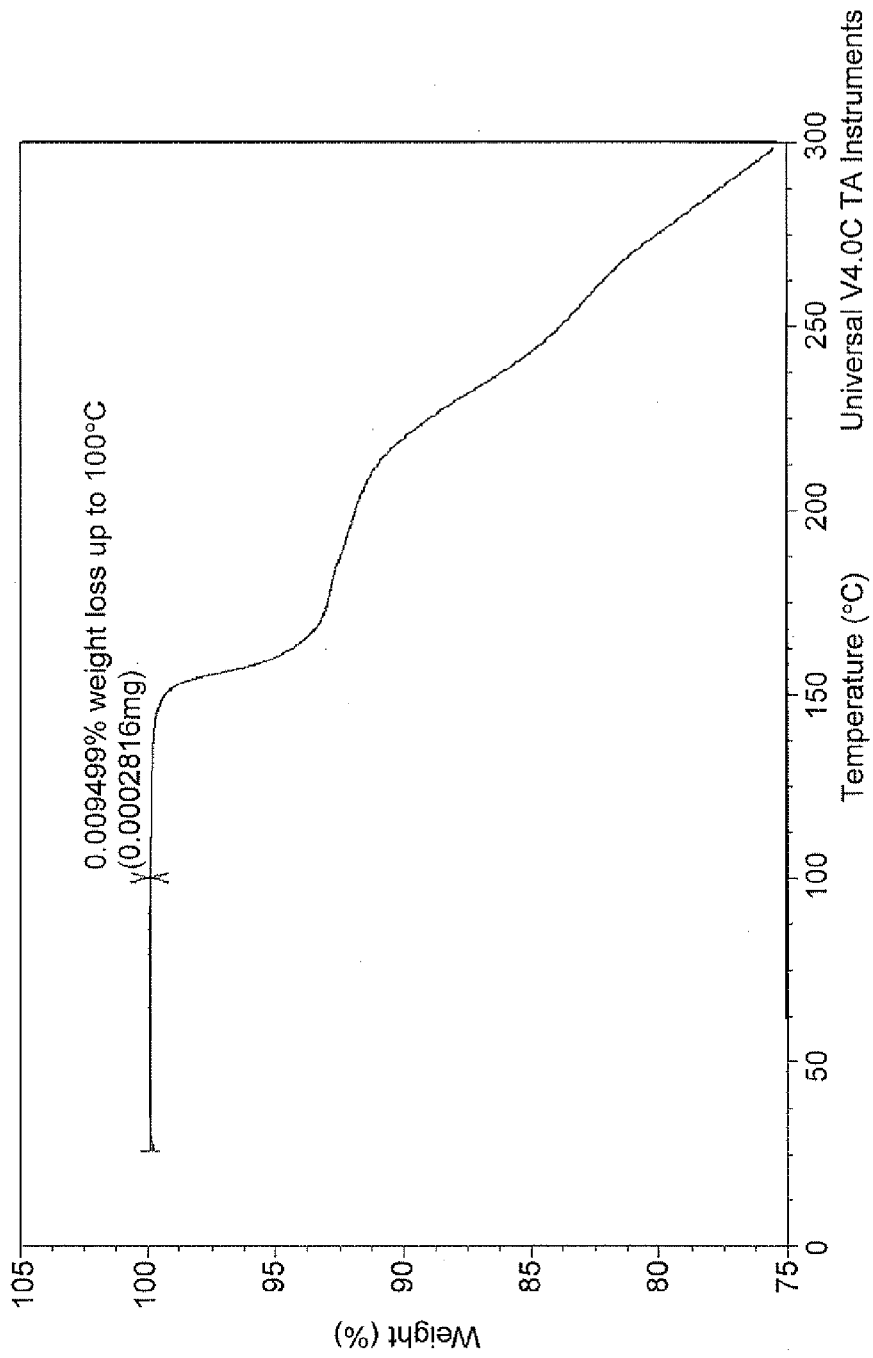
FIG. 5. TGA of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt), Form E-1.
Figure 6:
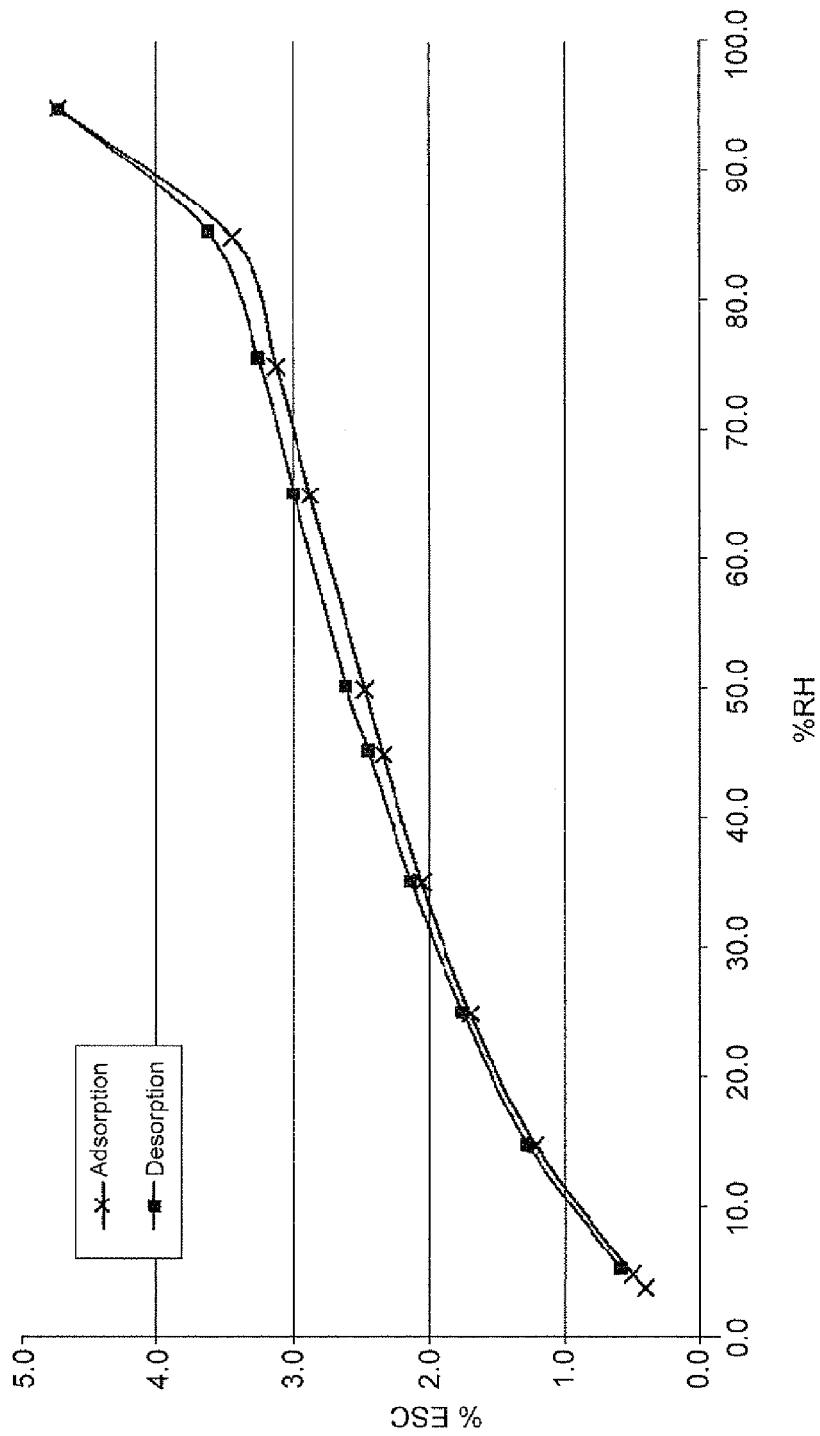
FIG. 6. Moisture-sorption isotherm analysis of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate, Form H-1.
Figure 7:
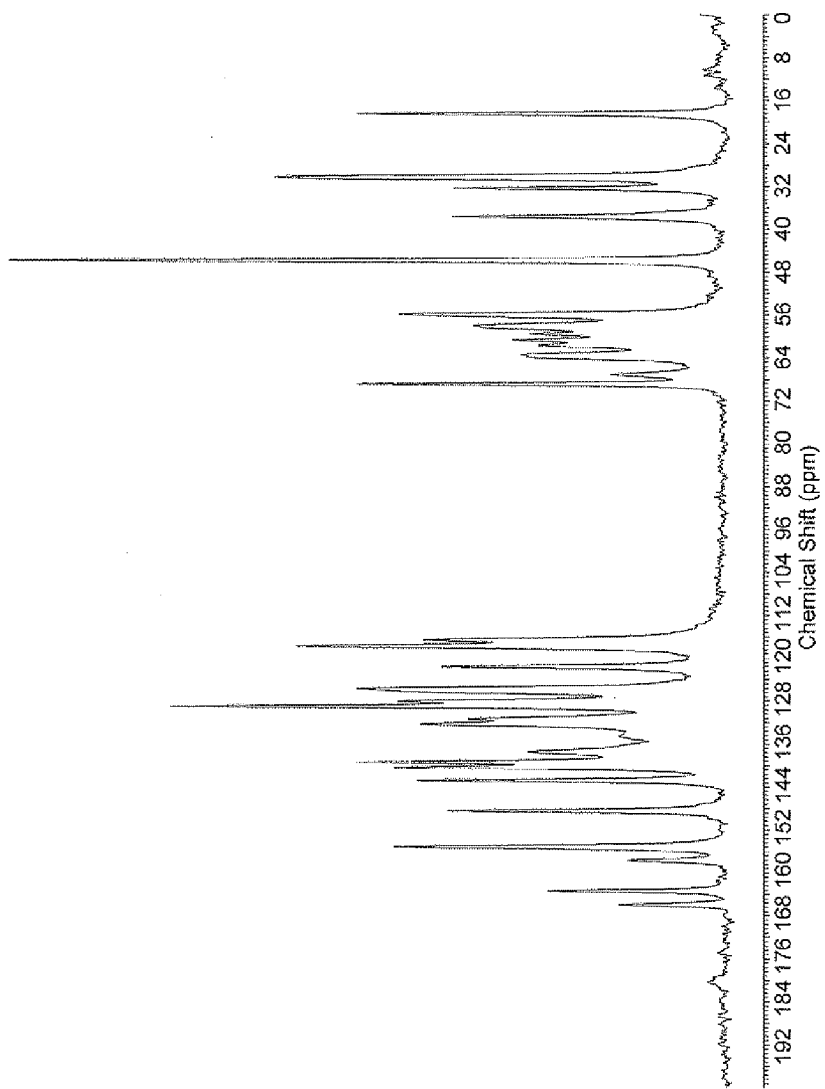
FIG. 7. $^{13}$C CPMAS ssNMR spectrum of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt), Form E-1.
Figure 8:
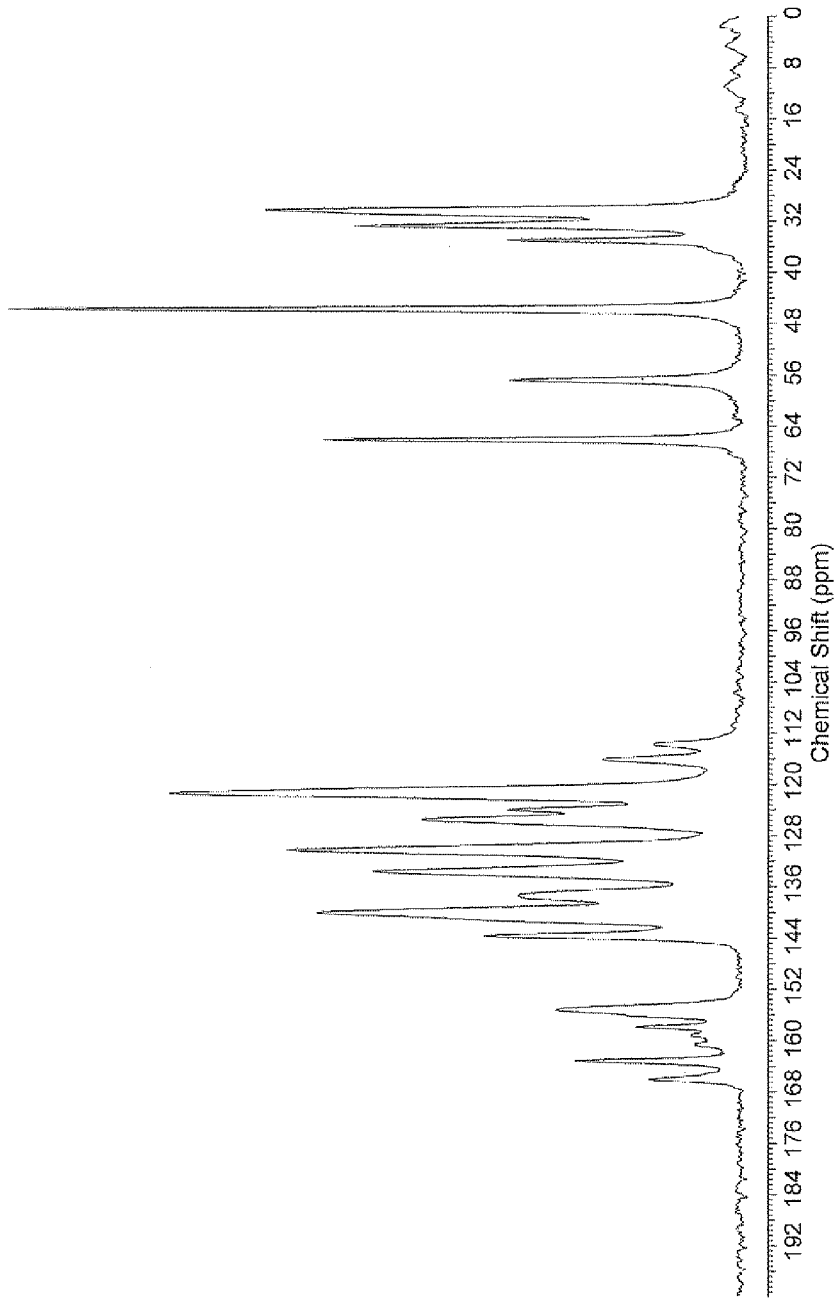
FIG. 8. $^{13}$C CPMAS ssNMR spectrum of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate, Form H-1.
Figure 9:
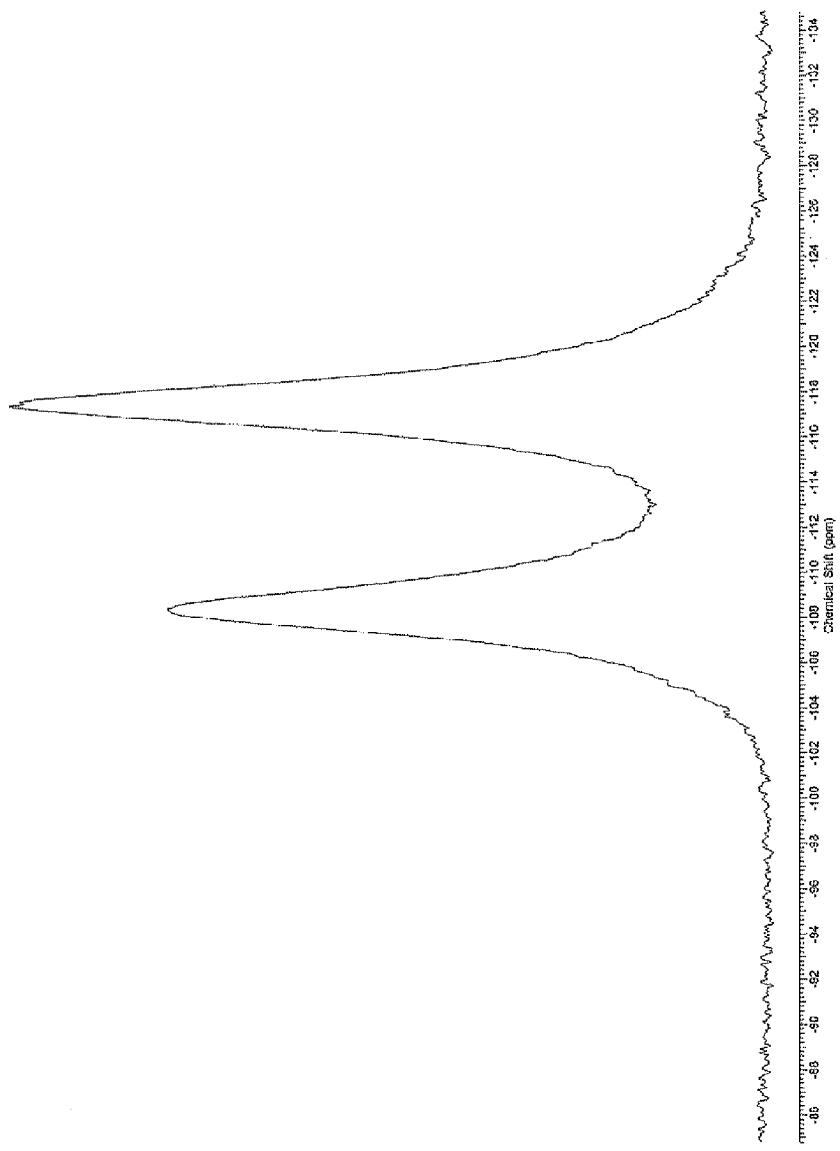
FIG. 9. $^{19}$F ssNMR spectrum of (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt), Form E-1.

Finally, FIGS. 2 and 3 present PXRD patterns for Forms E-1 and H-1, respectively. FIG. 4 discloses the DSC of Form E-1. FIG. 5 discloses the TGA of Form E-1. FIG. 6 discloses a moisture-sorption isotherm analysis of Form H-1. FIGS. 7 and 8 disclose the $^{13}$C CPMAS ssNMR spectra of Forms E-1 and H-1, respectively. FIG. 9 discloses the $^{19}$F ssNMR spectrum of Form E-1.

Form DSC and TGA Characterization

Form E-1, (4'-(2-(2-(2,6-dichlorophenyl)propan-2-yl)-4-(2-hydroxypropan-2-yl)-1H-imidazol-1-yl)-3,3'-difluoro-5-(methylsulfonyl)biphenyl-4-yl)methyl dihydrogen phosphate with 2-amino-2-(hydroxymethyl)propane-1,3-diol and ethanol (di-(2-amino-2-(hydroxymethyl)propanediol) ethanolate salt). Form E-1 was characterized by a DSC thermogram having an endothermic event typically at ca. 166° C., at higher temperatures other events may ensue. Form E-1 was characterized by a TGA curve having negligible weight loss at up to ca. 100° C.

TABLE 1

Unit Cell Parameters

| Form | T | a(Å) | b(Å) | C(Å) | α° | β° | γ° | Z' |
|---|---|---|---|---|---|---|---|---|
| H-1 | 25 | 9.793 (1) | 13.630 (2) | 24.189 (2) | 90.00 | 100.980 (5) | 90.00 | 1 |

| Form | V | Sg | Dcalc |
|---|---|---|---|
| H-1 | 3169.7 (6) | P2$_1$/n | 1.483 |

The variables used in Table 1 are defined below:
T = temperature in Centigrade for the crystallographic data;
Z' = number of drug molecules per asymmetric unit;
V = unit cell;
sg = space group;
dcalc = calculated crystal density.

TABLE 2

Fractional Atomic Coordinates for Form H-1, at T = 25° C.

| Atom | x | Y | Z | Atom | X | y | z |
|---|---|---|---|---|---|---|---|
| P | −0.06643 | 0.13527 | 0.51774 | C | 1.0503 | 0.3492 | 0.84030 |
| S | 0.12667 | 0.40608 | 0.63667 | O | −0.0201 | 0.4075 | 0.63263 |
| Cl | 0.88492 | 0.26573 | 0.73705 | C | 1.1821 | 0.2067 | 0.88667 |
| Cl | 0.97642 | 0.07116 | 0.94127 | C | 0.8215 | 0.0121 | 0.8457 |
| N | 1.0604 | 0.3027 | 0.97421 | C | 0.7600 | 0.0177 | 0.7897 |
| N | 0.8494 | 0.3030 | 0.92784 | O | 0.6670 | −0.0732 | 0.9898 |
| O | 0.0122 | 0.12112 | 0.46990 | C | 0.1632 | 0.3899 | 0.5699 |
| O | 0.05461 | 0.16414 | 0.56938 | H | 0.950428 | 0.400428 | 1.139350 |
| O | −0.1336 | 0.04128 | 0.53322 | H | 0.848167 | 0.334232 | 1.097447 |
| O | −0.1687 | 0.21700 | 0.50763 | H | 0.872586 | 0.443649 | 1.081869 |
| C | 0.5248 | 0.1974 | 0.84549 | H | 1.145096 | 0.280505 | 1.139312 |
| C | 0.8711 | 0.1712 | 0.78410 | H | 1.183955 | 0.251083 | 1.081588 |
| C | 0.6389 | 0.2130 | 0.88711 | H | 1.044876 | 0.213369 | 1.097194 |
| C | 0.7260 | 0.2919 | 0.88527 | H | 1.159226 | 0.297486 | 0.986773 |
| C | 0.3730 | 0.2440 | 0.75409 | H | 0.759378 | 0.348008 | 0.993235 |
| C | 0.2064 | 0.1356 | 0.70068 | H | 1.244821 | 0.255095 | 0.905980 |
| C | 1.0345 | 0.2509 | 0.87194 | H | 1.211819 | 0.187588 | 0.852629 |
| C | 0.9777 | 0.3331 | 1.01140 | H | 1.181750 | 0.150331 | 0.910450 |
| C | 0.9371 | 0.1722 | 0.84097 | H | 1.113942 | 0.391586 | 0.864297 |
| F | 0.1584 | 0.04232 | 0.69287 | H | 0.961488 | 0.380890 | 0.830345 |
| C | 0.1405 | 0.2073 | 0.66613 | H | 1.085707 | 0.335180 | 0.806765 |
| C | 0.4927 | 0.2631 | 0.80066 | H | 0.805819 | −0.043446 | 0.868072 |
| C | 0.5748 | 0.3458 | 0.80139 | H | 0.700667 | −0.033704 | 0.771700 |
| C | 0.9822 | 0.2829 | 0.92416 | H | 0.742225 | 0.102230 | 0.720536 |
| C | 0.3101 | 0.3193 | 0.71891 | H | 0.466610 | 0.141258 | 0.847350 |
| F | 0.6657 | 0.1543 | 0.93122 | H | 0.551436 | 0.394052 | 0.772200 |

TABLE 2-continued

Fractional Atomic Coordinates for Form H-1, at T = 25° C.

| Atom | x | Y | Z | Atom | X | y | z |
|---|---|---|---|---|---|---|---|
| C | 0.3189 | 0.1506 | 0.74349 | H | 0.360202 | 0.096828 | 0.766364 |
| C | 0.8467 | 0.3325 | 0.98283 | H | 0.345054 | 0.385112 | 0.724314 |
| C | 1.0340 | 0.3547 | 1.07276 | H | 0.743044 | 0.420034 | 0.843970 |
| C | 0.6893 | 0.3609 | 0.84358 | H | −0.051531 | 0.236622 | 0.618008 |
| C | 0.1979 | 0.3011 | 0.67609 | H | −0.031332 | 0.125231 | 0.633572 |
| O | 1.1247 | 0.4385 | 1.07924 | H | 0.127740 | 0.444301 | 0.546228 |
| C | 0.7857 | 0.0963 | 0.75946 | H | 0.121509 | 0.330240 | 0.553714 |
| C | 0.9081 | 0.0864 | 0.86948 | H | 0.262317 | 0.386268 | 0.573043 |
| C | 1.1088 | 0.2674 | 1.10029 | H | 1.199601 | 0.426864 | 1.059565 |
| O | 0.2021 | 0.4888 | 0.66121 | H | 0.053976 | 0.057152 | 0.472827 |
| C | 0.0128 | 0.1828 | 0.62230 | H | 0.619917 | −0.065784 | 0.951475 |
| C | 0.9155 | 0.3861 | 1.10037 | H | 0.675817 | −0.141784 | 0.999075 |

TABLE 3

Characteristic powder x-ray diffraction peak positions (degrees 2θ ± 0.1)@ RT for Forms E-1 and H-1 based on a high quality pattern collected with a diffractometer (CuKα) with a spinning capillary with 2θ calibrated with a NIST other suitable standard.

| Form E-1 | Form H-1 |
|---|---|
| 7.5 | 7.4 |
| 9.2 | 12.4 |
| 10.4 | 13.0 |
| 11.9 | 14.6 |
| 15.8 | 18.5 |
|  | 22.4 |
|  | 23.7 |

TABLE 4

SSNMR Peak Positions/δ (in ppm) Relative to TMS (Tetramethyl Silane) Determined at 280° K

| Form E-1 δ/ppm | Form H-1 δ/ppm |
|---|---|
| 18 | 30 |
| 30 | 33 |
| 31 | 35 |
| 32 | 46 |
| 38 | 57 |
| 46 | 66 |
| 56 | 114 |
| 56 | 116 |
| 58 | 122 |
| 58 | 124 |
| 60 | 126 |
| 61 | 130 |
| 62 | 134 |
| 63 | 137 |
| 64 | 140 |
| 67 | 144 |
| 69 | 155 |
| 117 | 158 |
| 118 | 159 |
| 122 | 161 |
| 126 | 163 |
| 126 | 166 |
| 128 |  |
| 129 |  |
| 131 |  |
| 132 |  |
| 135 |  |
| 136 |  |
| 138 |  |
| 139 |  |
| 140 |  |
| 143 |  |
| 149 |  |
| 155 |  |
| 158 |  |
| 163 |  |
| 166 |  |

These data are strictly valid for a 400 MHz spectrophotometer.

Utility

The compounds of the invention, preferably Examples 1, 3, 4, 6 and 7, more preferably, Examples 1, 3, and 4, and Forms E-1 and H-1, exhibit valuable pharmacological properties. The compounds of the invention are useful for the treatment of diseases or disorders described herein, such as those associated with, or having symptoms arising from the complications of, altered cholesterol transport, reverse cholesterol transport, fatty acid metabolism, cholesterol absorption, cholesterol re-absorption, cholesterol secretion, cholesterol excretion, or cholesterol metabolism.

These diseases include, for example, atherosclerosis, atherosclerotic cardiovascular diseases, (see, e.g., PCT Publication Nos. WO 00/57915 and WO 00/37077), dyslipidemia, hyperglycemia, insulin resistance, diabetes, obesity, syndrome X (U.S. Patent Application Publication No. 2003/0073614, PCT Publication No. WO 01/82917), excess lipid deposition in peripheral tissues such as skin (xanthomas) (see, e.g., U.S. Pat. Nos. 6,184,215 and 6,187,814), stroke, peripheral occlusive disease, memory loss (*Brain Res.*, 752: 189-196 (1997)), optic nerve and retinal pathologies (i.e., macular degeneration, retinitis pigmentosa), repair of traumatic damage to the central or peripheral nervous system (*Trends in Neurosciences*, 17:525-530 (1994)), prevention of the degenerative process due to aging (*Am. J. Pathol.*, 151: 1371-1377 (1997)), or Alzheimer's disease (see, e.g., PCT Publication No. WO 00/17334; *Trends in Neurosciences*, 17:525-530 (1994)), prevention of degenerative neuropathies occurring in diseases such as diabetic neuropathies (see, e.g., PCT Publication No. WO 01/82917), multiple sclerosis (*Ann. Clin. Biochem.*, 33(2):148-150 (1996)), and autoimmune diseases (*J. Lipid Res.*, 39:1740-1743 (1998)).

Also provided, are methods of increasing the expression of ATP-Binding Cassette (ABCA1), (see, e.g., PCT Publication No. WO 00/78972) thereby increasing reverse cholesterol transport in mammalian cells using the claimed compounds and compositions.

Accordingly in another aspect, the invention also includes methods to remove cholesterol from tissue deposits such as atherosclerotic plaques or xanthomas in a subject with atherosclerosis or atherosclerotic cardiovascular disease manifest by clinical signs of such disease, wherein the methods comprise administering to the subject a therapeutically effective amount of a compound, preferably Examples 1, 3, 4, 6 and 7, more preferably, Examples 1, 3, and 4, and Forms E-1 and H-1, or a composition comprising a compound, preferably Examples 1, 3, 4, 6 and 7, more preferably, Examples 1, 3, and 4, and Forms E-1 and H-1, of the present invention. Additionally, the instant invention also provides a method for preventing or reducing the risk of a first or subsequent occurrence of an atherosclerotic cardiovascular disease event including ischemic heart disease, ischemic stroke, multi-infarct dementia, and intermittent claudication comprising the administration of a prophylactically effective amount of a compound, preferably Examples 1, 3, 4, 6 and 7, more preferably, Examples 1, 3, and 4, and Forms E-1 and H-1, or a composition comprising a compound, preferably Examples 1, 3, 4, 6 and 7, more preferably, Examples 1, 3, and 4, and Forms E-1 and H-1, of the present invention to a subject at risk for such an event.

The compounds of the present invention, preferably Examples 1, 3, 4, 6 and 7, more preferably, Examples 1, 3, and 4, and Forms E-1 and H-1, can also be used in methods for decreasing hyperglycemia and insulin resistance, i.e., in methods for treating diabetes (PCT Publication No. WO 01/82917), and in methods of treatment, prevention, or amelioration of disorders related to, or arising as complications of diabetes, hyperglycemia or insulin resistance including the cluster of disease states, conditions or disorders that make up "Syndrome X" (See U.S. Patent Application Publication No. 2003/0073614) comprising the administration of a therapeutically effective amount of a compound or composition of the present invention to a subject in need of such treatment. Additionally, the instant invention also provides a method for preventing or reducing the risk of developing hyperglycemia, insulin resistance, diabetes or syndrome X in a subject, comprising the administration of a prophylactically effective amount of a compound or composition of the present invention to a subject at risk for such an event.

Diabetes mellitus, commonly called diabetes, refers to a disease process derived from multiple causative factors and characterized by elevated levels of plasma glucose, referred to as hyperglycemia. See, e.g., LeRoith, D. et al., eds., *Diabetes Mellitus*, Lippincott-Raven Publishers, Philadelphia, Pa., USA (1996). Uncontrolled hyperglycemia is associated with increased and premature mortality due to an increased risk for macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM). Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese subjects and lipid oxidation is increased.

Premature development of atherosclerosis and an increased rate of cardiovascular and peripheral vascular diseases are characteristic features of subjects with diabetes. Hyperlipidemia is an important precipitating factor for these diseases. Hyperlipidemia is a disorder generally characterized by an abnormal increase in serum lipids, e.g., cholesterol and triglyceride, in the bloodstream and is an important risk factor in developing atherosclerosis and heart disease. For a review of disorders of lipid metabolism, see, e.g., Wilson, J. et al., eds., Chapter 23: "Disorders of Lipid Metabolism", *Textbook of Endocrinology*, 9th Edition, W.B. Sanders Company, Philadelphia, Pa., USA (1998).

Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E., *Ann. Chim. Med.*, 5:1061-1079 (1927)). Epidemiological studies since then have confirmed the association and have shown a several-fold increase in coronary deaths among diabetic subjects when compared with non-diabetic subjects (see, e.g., Garcia, M. J. et al., *Diabetes*, 23:105-111 (1974); and Laakso, M. et al., *Diabetes Rev*, 5(4):294-315 (1997)). Several lipoprotein abnormalities have been described among diabetic subjects (Howard B. et al., *Arteriosclerosis*, 30:153-162 (1978)).

Further provided by this invention are methods of using the compounds of the invention, preferably Examples 1, 3, 4, 6 and 7, more preferably, Examples 1, 3, and 4, and Forms E-1 and H-1, to treat obesity, as well as the complications of obesity. Obesity is linked to a variety of medical disorders including diabetes and hyperlipidemia. Obesity is also a known risk factor for the development of type 2 diabetes (See, e.g., Barrett-Conner, E., *Epidemol. Rev.*, 11:172-181 (1989); and Knowler, et al., *Am. J. Clin. Nutr.*, 53:1543-1551 (1991)).

Compounds within the scope of the present invention alter nuclear receptor activity, including LXR and/or orphan nuclear receptor activity, and as such are useful in the treatment, prevention, or amelioration of one or more symptoms of diseases or disorder that are modulated by nuclear receptor activity, including LXR and/or orphan nuclear receptor activity, or in which nuclear receptor activity, including LXR and/or orphan nuclear receptor activity, is implicated.

The present invention thus provides methods for the prevention or treatment of one or more of the aforementioned disorders, comprising the step of administering to a subject in need thereof an effective amount of at least one compound of the present invention, preferably Examples 1, 3, 4, 6, 7 and 9, more preferably, Examples 1, 3 and 4. Other therapeutic agents such as those described below may be employed with the inventive compounds, preferably Examples 1, 3, 4, 6 and 7, more preferably, Examples 1, 3, and 4, and Forms E-1 and H-1, in the present methods. In the methods of the present invention, such other therapeutic agent(s) may be administered prior to, simultaneously with or following the administration of the compound(s) of the present invention.

Standard physiological, pharmacological and biochemical procedures are available for testing the compounds to identify those that possess biological activities that modulate the activity of the LXRs (LXR$_\alpha$ and LXR$_\beta$). Such assays include, for example, biochemical assays such as binding assays, fluorescence polarization assays, FRET-based coactivator recruitment assays (see, generally, Glickman et al., *J. Biomolecular Screening*, 7(1):3-10 (2002)), as well as cell based assays including the co-transfection assay, the use of LBD-Gal 4 chimeras and protein-protein interaction assays, (see, Lehmann et al., *J. Biol. Chem.*, 272(6):3137-3140 (1997)).

Pharmacokinetic Study

Pharmacokinetic profiles of compounds of the present invention were evaluated in male beagle dogs (8.8-11.1 kg). IV and PO (solution or suspension) studies were conducted in a crossover design (N=3). There was at least a one week washout period between the IV and the PO studies. Animals with chronically implanted vascular access ports in the femoral vein were used for administration of the IV dose. Dogs were fasted overnight prior to oral dosing and were fed 4 hours after dosing. In the IV study, the compound of the present invention was infused at 1 mg/kg (1 mg/mL in 90% PEG 400/10% Ethanol) over 10 min at a constant rate of 1 mL/min. In the PO studies, the compounds were administered by oral gavage at 1 mg/kg (1 mg/mL) in 90% PEG 400/10% Ethanol (as a solution) or in 0.5% carboxyl methylcellulose in capsule (as a suspension) to pentagastrin-pretreated dogs. In a subsequent study, the effect of pH on the oral bioavailability was investigated by administering a compound of the present invention (0.1 or 1 mg/kg) as a suspension dose in capsule to the same dogs after famotidine pretreatment. Serial blood samples were collected by direct jugular venipuncture at 0.25, 0.5, 0.75, 1, 2, 4, 6, 8, 24 and 48 hours post-dose. Plasma was prepared immediately, and the samples were frozen on dry ice. Additionally urine and feces (only PO arm) were collected on ice over the 48 hour post dose from each dog and urine volumes were recorded. Plasma, feces and urine samples were stored at −20° C. until analysis. Aliquots of urine and feces samples were analyzed for the compounds.

The pharmacokinetic parameters of a compound of the present invention were obtained by non-compartmental analysis of plasma concentration vs. time data (KINETICA software, Version 4.2, InnaPhase Corporation, Philadelphia, Pa.). The peak concentration (Cmax) and time for Cmax (Tmax) were recorded directly from experimental observations. The area under the curve from time zero to the last sampling time (AUC(0-T)) and the area under the curve from time zero to infinity (AUC(INF)) were calculated using a combination of linear and log trapezoidal summations. The total plasma clearance (CLTp), steady-state volume of distribution (Vss), apparent elimination half-life (T1/2) and mean residence time (MRT) were estimated after IV administration. Estimations of AUC and T1/2 were made using a minimum of 3 time points with quantifiable concentrations. The total blood clearance (CLTb) was calculated as the CLTp divided by the blood-to-plasma concentration ratio. The absolute oral bioavailability (F) was estimated as the ratio of dose-normalized AUC values following oral and IV doses. Recovery in urine and feces was calculated as the cumulative amount of unchanged drug recovered in each biological sample divided by the dose administered.

The pharmacokinetic parameters of compounds of the present invention were determined in the manner described above and the results shown in Table 5 below were obtained.

TABLE 5

| Compound | Structure | Pretreatment | Dose (mg/kg) | AUC0 −48 H (μM.h) | % F* |
|---|---|---|---|---|---|
| Example 9 PCT Publication No. WO 2010/138598 | 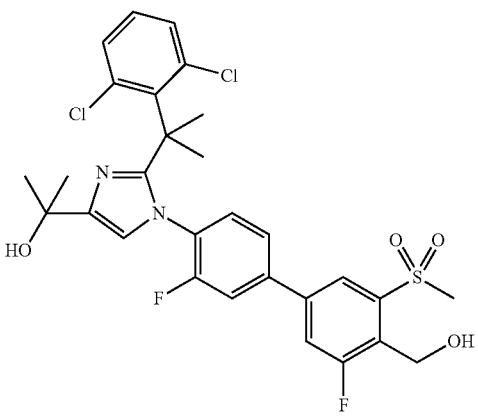 [SMILES: CC(C)(O)c1cn(-c2ccc(-c3cc(F)c(CO)c(S(C)(=O)=O)c3)cc2F)c(C(C)(C)c2c(Cl)cccc2Cl)n1] | pentagastrin | 1.0 | 3.6 | 72 |

TABLE 5-continued

| Compound | Structure | Pretreatment | Dose (mg/kg) | AUC0–48 H (μM.h) | % F* |
|---|---|---|---|---|---|
| Example 9 PCT Publication No. WO 2010/138598 | 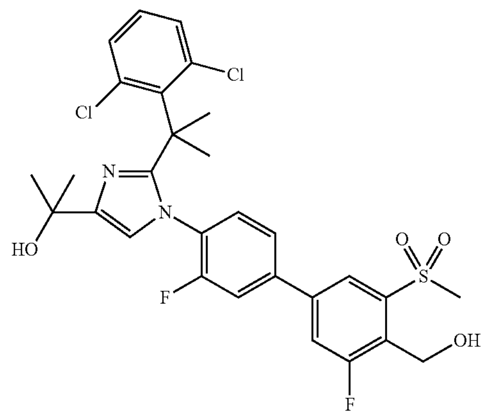 [SMILES: CC(C)(O)c1cn(-c2ccc(-c3cc(F)c(CO)c(S(C)(=O)=O)c3)cc2F)c(C(C)(C)c2c(Cl)cccc2Cl)n1] | Famotidine | 1.0 | 0.6 | 14 |
| Example 1 Present Invention | | pentagastrin | 1.0 | 3.8 | 61 |
| Example 1 Present Invention | | Famotidine | 1.0 | 6.0 | 98 |

TABLE 5-continued

| Compound | Structure | Pretreatment | Dose (mg/kg) | AUC0−48 H (μM.h) | % F* |
|---|---|---|---|---|---|
| Example 4 Present Invention | *(structure)* | pentagastrin | 1.0 | 3.8 | 82 |
| Example 4 Present Invention | *(structure)* | Famotidine | 1.0 | 6.7 | 145 |
| Example 7 Present Invention | *(structure)* | Famotidine | 1.0 | 1.6 | — |

*Relative to IV administration of Examples 1 and 4 of the present invention to the same dogs.

The above data clearly demonstrates the surprising improvement in bioavailability of a parent compound in dogs treated with famotidine via the compounds of the present invention.

pH-Solubility Study

An excess of test compound, for example, (4'-(2-(1-(2,6-dichlorophenyl)-1-methylethyl)-4-(1-hydroxy-1-methylethyl)-1H-imidazol-1-yl)-3,3'-difluoro-5-(methylsulfonyl)biphenyl-4-yl)methyl dihydrogen phosphate, was agitated with 0.05 M constant ionic strength ($\mu$=0.15) aqueous buffers in the pH range of 1-9. The 2.0 mL samples were agitated for 24 hours at rt in 5 mL vials using a bench top rotator. Following agitation, the samples were filtered. The filtrate was diluted if necessary and assayed by RP-HPLC.

The pH solubility profile of a compound of the present invention and its parent compound were determined in the manner described immediately above and the results shown in FIG. 1 were obtained.

In addition, various animal models exist for a number of diseases of direct relevance to the claimed compounds, which can be used to further profile and characterize the claimed compounds. For example, model systems including diabetic dislipidemia using Zucker (fa/fa) rats or (db/db) mice, spontaneous hyperlipidemia using apolipoprotein E deficient mice (ApoE.sup.−/−), diet-induced hyperlipidemia, using low density lipoprotein receptor deficient mice (LDLR.sup.−/−) and atherosclerosis using both the Apo E(.sup.−/−) and LDLR (.sup.−/−) mice fed a western diet. (21% fat, 0.05% cholesterol) may be used. Additionally LXR animal models (e.g., knockout mice) can be used to further evaluate the present compounds and compositions in vivo (see, for example, Peet et al., Cell, 93:693-704 (1998), Sinal et al., Cell, 102:731-744 (2000)). Additionally compounds of the invention can be tested in mice, hamsters, rabbits or cynomolgus monkeys for peripheral blood cell ABCA1 and ABCG1 gene inductions and lipid effects.

The present invention also provides pharmaceutical compositions comprising at least one of the compounds of the present invention, preferably Examples 1, 3, 4, 6 and 7, more preferably, Examples 1, 3 and 4, and Forms E-1 and H-1, and the salts of such compounds capable of preventing, treating, and/or slowing the progression of one or more of the aforementioned disorders in an amount effective therefore, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

A compound of the invention can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumor, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

A compound of the invention can be administered in any acceptable solid, semi-solid, liquid or gaseous dosage form. Acceptable dosage forms include, but are not limited to, aerosols, capsules, creams, emulsions, gases, gels, grains, liniments, lotions, ointments, pastes, powders, solutions, suspensions, syrups and tablets. Acceptable delivery systems include, but are not limited to, biodegradable implants (e.g., poly(DL-lactide), lactide/glycolide copolymers and lactide/caprolactone copolymers), capsules, douches, enemas, inhalers, intrauterine devices, nebulizers, patches, pumps and suppositories.

A dosage form of the invention may be comprised solely of a compound of the invention, preferably Examples 1, 3, 4, 6 and 7, more preferably, Examples 1, 3 and 4, and Forms E-1 and H-1, or the compound of the invention may be formulated along with conventional excipients, pharmaceutical carriers, adjuvants, and/or other medicinal or pharmaceutical agents. Acceptable excipients include, but are not limited to: (a) antiadherents, such as croscarmellose sodium, crosprovidone, sodium starch glycolate, microcrystalline cellulose, starch and talc; (b) binders, such as cellulose, gelatin, hydroxypropyl cellulose, lactose, maltitol, polyethylene glycol, polyvinyl pyrrolidone, sorbitol, starch, sugar, sucrose and xylitol; (c) coatings, such as cellulose, shellac, zein and enteric agents; (d) disintegrants, such as cellulose, crosslinked polyvinyl pyrrolidone, sodium carboxymethylcellulose, methylcellulose, microcrystalline cellulose, sodium starch glycolate and starch; (e) filling agents, such as calcium carbonate, cellulose, dibasic calcium phosphate, glucose, lactose, mannitol, sorbitol and sucrose; (f) flavoring agents; (g) coloring agents; (h) glidants, such as calcium stearate, colloidal silicon dioxide, glyceryl behenate, glyceryl monostearate, glyceryl palmitostearate, hydrogenated vegetable oil, magnesium stearate, magnesium trisilicate, mineral oil, polyethylene glycols, silicon dioxide, starch, stearate, stearic acid, talc, sodium stearyl fumarate, sodium benzoate and zinc; (i) lubricants, such as calcium stearate, hydrogenated vegetable oils, magnesium stearate, mineral oil, polyethylene glycol, sodium stearyl fumarate, stearin, stearic acid and talc; and (j) preservatives, such as chlorobutanol, citric acid, cysteine, methionine, methyl paraben, phenol, propyl paraben, retinyl palmitate, selenium, sodium citrate, sorbic acid, vitamin A, vitamin C and vitamin E. Capsules may contain any of the afore listed excipients, and may additionally contain a semi-solid or liquid carrier, such as a polyethylene glycol or vegetable-based oils. Pharmaceutical carriers include soluble polymers, microparticles made of insoluble or biodegradable natural and synthetic polymers, microcapsules or microspheres, lipoproteins, liposomes and micelles.

The pharmaceutical composition may be in the form of a liquid, e.g., an elixir, syrup, solution, emulsion, suspension, or other like forms or may be presented as a dry product for reconstitution with water or other suitable vehicle before use. Liquid preparations may contain conventional additives such as: (a) liquid diluents, such as water, saline, Ringer's solution, fixed oils such as synthetic mono or diglycerides, or polyethylene glycols, glycerin, propylene glycol or other solvents; (b) surfactants, suspending agents, or emulsifying agents, such as polyoxyethylene sorbitan fatty acid esters, saturated polyglycolized glycerides, monoglycerides, fatty acid esters, block copolymers of ethylene oxide and propylene oxide, polyoxyl stearates, ethoxylated castor oils, and ethoxylated hydroxystearic acids; (c) buffers, such as acetates, citrates or phosphates; (d) chelating agents, such as ethylenediaminetetraacetic acid; (e) antibacterial agents, such as benzyl alcohol or methyl paraben; (f) antioxidants, such as ascorbic acid or sodium bisulfate; and (g) isotonic agents, sodium chloride or dextrose; as well as sweetening and flavoring agents, dyes and preservatives.

A pharmaceutical composition of the invention will contain a therapeutically effective amount of a compound of the invention, preferably Examples 1, 3, 4, 6 and 7, more preferably, Examples 1, 3, and 4, and Forms E-1 and H-1, as an individual stereoisomer or mixture of stereoisomers, or a pharmaceutically acceptable salt thereof, with the remainder of the pharmaceutical composition comprised of one or more pharmaceutically acceptable excipients. Generally, for oral administration, a compound of the invention, as an individual stereoisomer or mixture of stereoisomers, or a pharmaceutically acceptable salt thereof will comprise from 1% to 99% by weight of a pharmaceutically acceptable composition, with the remainder of the composition comprised of one or more pharmaceutically acceptable excipients. Typically, a compound of the invention, as an individual stereoisomer or mixture of stereoisomers, or a pharmaceutically acceptable salt thereof will comprise from 5% to 75% by weight of a pharmaceutically acceptable composition, with the remainder of the composition comprised of one or more pharmaceutically acceptable excipients. For parenteral administration, a compound of the invention, as an individual stereoisomer or mixture of stereoisomers, or a pharmaceutically acceptable salt thereof will comprise from 0.01% to 1% by weight of a pharmaceutically acceptable composition. Methods for preparing the dosage forms of the invention are known, or will be apparent, to those skilled in this art; for example, see *Remington's Pharmaceutical Sciences,* 18th Edition, Mack Publishing Company, Easton, Pa. (1990).

A therapeutically effective amount of a compound of the invention will vary depending upon a sundry of factors including the activity, metabolic stability, rate of excretion and duration of action of the compound, the age, weight, general health, sex, diet and species of the subject, the mode and time of administration of the compound, the presence of adjuvants or additional therapeutically active ingredients in a composition, and the severity of the disease for which the therapeutic effect is sought.

The compounds of the invention can be administered to human subjects at dosage levels in the range of about 0.1 to about 10,000 mg per day. A normal human adult having a body weight of about 70 kilograms can be administered a dosage in the range of from about 0.15 µg to about 150 mg per kilogram of body weight per day. Typically, a normal adult human will be administered from about 0.1 mg to about 25 mg, or 0.5 mg to about 10 mg per kilogram of body weight per day. The compounds of the invention may be administered in one or more unit dose forms. The unit doses may be administered one to four times a day, or two times a day, or once a day. In an alternate method of describing an effective dose, an oral unit dose is one that is necessary to achieve a blood serum level of about 0.02 to 20 µg/ml or about 1 to 20 µg/ml in a subject. The optimum dose of a compound of the invention for a particular subject can be determined by one of ordinary skill in the art.

Compounds of the invention, or an individual isomer or mixture of isomers or a pharmaceutically acceptable salt thereof, may also be administered simultaneously with, prior to, or after administration of one or more of the therapeutic agents described below. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an HMG-CoA reductase inhibitor can be administered to the subject together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In one embodiment, the compounds of the invention are used in combination with one or more of the following therapeutic agents in treating atherosclerosis: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A:cholesterol acyltransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin or fabric acid derivatives.

In another embodiment, the compounds of the invention, preferably Examples 1, 3, 4, 6 and 7, more preferably, Examples 1, 3, and 4, and Forms E-1 and H-1, are used in combination with one or more of the following therapeutic agents in treating cholesterol biosynthesis inhibitor, particularly an HMG-CoA reductase inhibitor. The term HMG-CoA reductase inhibitor is intended to include all pharmaceutically acceptable salt, ester, and other forms of compounds which have HMG-CoA reductase inhibitory activity and, therefore, the use of such salts, esters, and other forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®; see, U.S. Pat. No. 5,273,995) and rivastatin (also known as cerivastatin; see, U.S. Pat. No. 5,177,080). The structural formulae of these and additional HMG-CoA reductase inhibitors that can be used in combination with the compounds of the invention are described at page 87 of Yalpani, M., "Cholesterol Lowering Drugs", *Chemistry & Industry,* 85-89 (Feb. 5, 1996). In presently preferred embodiments, the HMG-CoA reductase inhibitor is selected from lovastatin and simvastatin.

In an additional embodiment, the compounds of the invention, preferably Examples 1, 3, 4, 6 and 7, more preferably, Examples 1, 3, and 4, and Forms E-1 and H-1, are used in combination with one or more of the following therapeutic agents in treating with one or more additional active diabetes agents depending on the desired target therapy (see, e.g., Turner, N. et al., *Prog. Drug Res.,* 51:33-94 (1998); Haffner, S., *Diabetes Care,* 21:60-178 (1998); and DeFronzo, R. et al., eds., *Diabetes Reviews,* 5(4) (1997)). A number of studies have investigated the benefits of combination therapies with oral agents (see, e.g., Mahler, R., *J. Clin. Endocrinol. Metab.,* 84:1165-1171 (1999); United Kingdom Prospective Diabetes Study Group: UKPDS 28, *Diabetes Care,* 21:87-92 (1998); Bardin, C. W., ed., *Current Therapy in Endocrinology and Metabolism,* 6th Edition, Mosby-Year Book, Inc., St. Louis, Mo. (1997); Chiasson, J. et al., *Ann. Intern. Med.,* 121:928-935 (1994); Coniff, R. et al., *Clin. Ther.,* 19:16-26 (1997); Coniff, R. et al., *Am. J. Med.,* 98:443-451 (1995); Iwamoto, Y. et al., *Diabet. Med.,* 13:365-370 (1996); Kwiterovich, P., *Am. J. Cardiol.,* 82(12A):3U-17U (1998)). These studies indicate that diabetes and hyperlipidemia modulation can be further improved by the addition of a second agent to the therapeutic regimen.

In a further embodiment, the compounds of the invention, preferably Examples 1, 3, 4, 6 and 7, more preferably, Examples 1, 3 and 4, and Forms E-1 and H-1, are used in combination with one or more of the following therapeutic agents in treating in treating diabetes: sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO4); antiglucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

In yet another embodiment, the compounds of the invention, preferably Examples 1, 3, 4, 6 and 7, more preferably, Examples 1, 3 and 4, and Forms E-1 and H-1, are used in combination with one or more of the following therapeutic agents in treating obesity or obesity-related disorders. Such agents, include, but are not limited to, phenylpropanolamine, phentermine, diethylpropion, mazindol, fenfluramine, dexfenfluramine, phentiramine, $\beta_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

All of the above referenced patents and patent applications are hereby incorporated by reference herein.

The combinations can be co-formulated or in the form of kits packaged to provide appropriate dosages for co-administration.

The above other therapeutic agents, when employed in combination with the compounds of the present invention, may be used, for example, in those amounts indicated in the *Physicians' Desk Reference* (PDR) or as otherwise determined by one of ordinary skill in the art.

All publications, patents, and patent applications cited herein are hereby incorporated herein by reference for all purposes.

What is claimed is:

1. A compound, or pharmaceutically acceptable salt thereof, selected from the group consisting of:

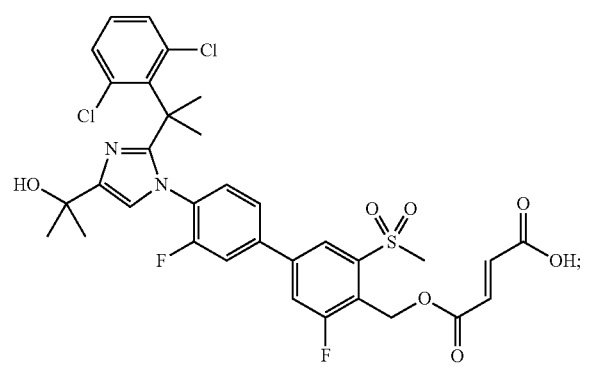

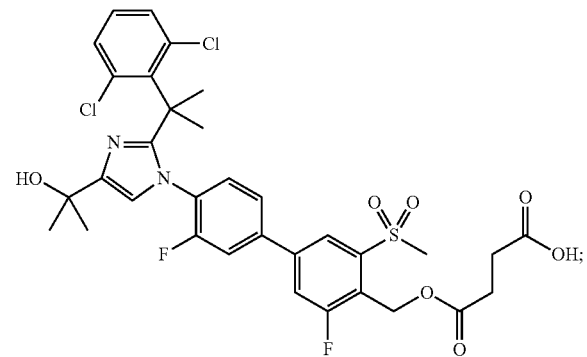

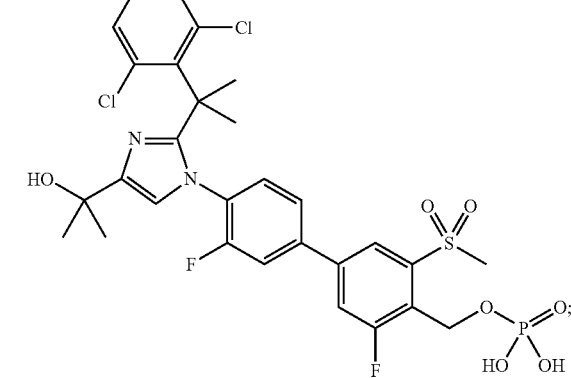

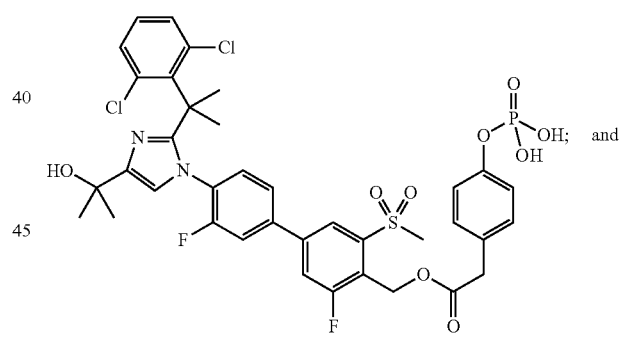

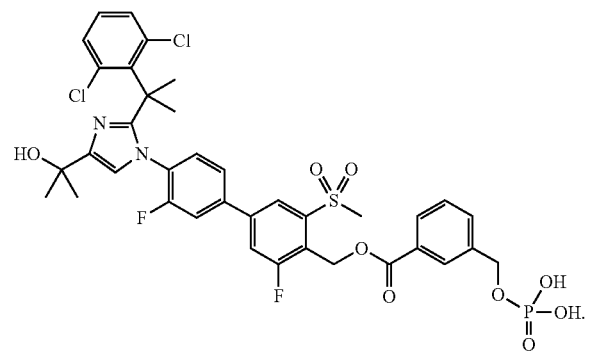

2. A compound, or pharmaceutically acceptable salt thereof, of claim 1 which is

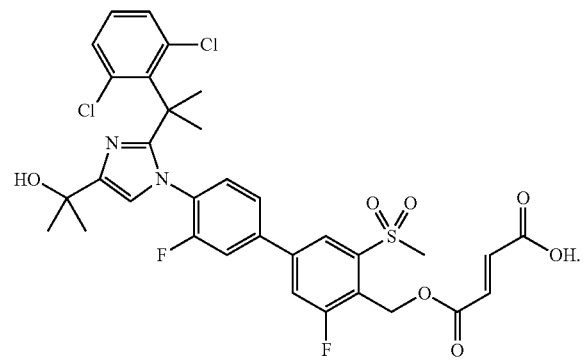 [SMILES: CC(C)(O)c1cn(-c2ccc(-c3cc(F)c(COC(=O)/C=C/C(=O)O)c(S(C)(=O)=O)c3)cc2F)c(C(C)(C)c2c(Cl)cccc2Cl)n1]

3. A compound, or pharmaceutically acceptable salt thereof, of claim 1 which is

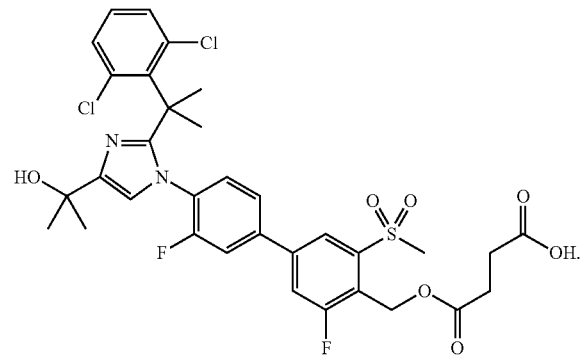

4. A compound, or pharmaceutically acceptable salt thereof, which is

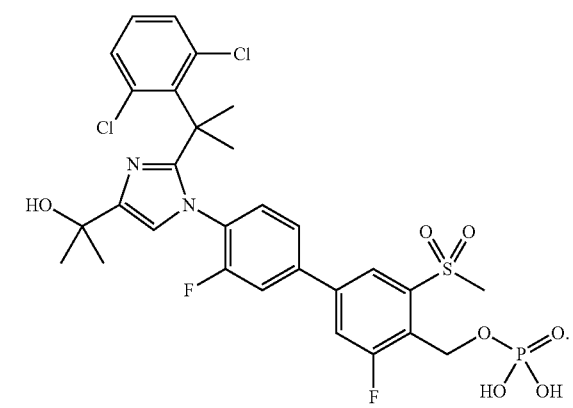 [SMILES: CC(C)(O)c1cn(-c2ccc(-c3cc(F)c(COP(=O)(O)O)c(S(C)(=O)=O)c3)cc2F)c(C(C)(C)c2c(Cl)cccc2Cl)n1]

5. A compound, or pharmaceutically acceptable salt thereof, which is

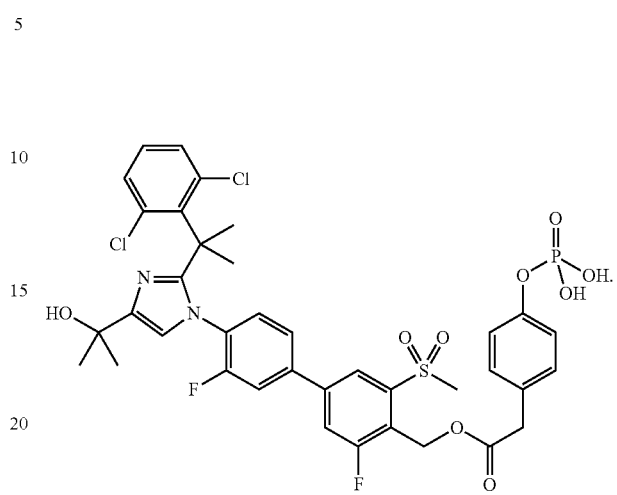

6. The compound of claim 4 that is a pharmaceutically acceptable salt of said compound.

7. The compound of claim 6, wherein the pharmaceutically acceptable salt comprises the di-(2-amino-2-(hydroxymethyl)propanediol)ethanolate salt.

8. A composition comprising at least one compound of claim 1 and one or more pharmaceutically acceptable carriers.

9. The composition of claim 8 further comprising at least one additional therapeutic agent.

10. A method of treating a disease or disorder comprising administering to a subject in need thereof a therapeutically effective amount of at least one compound of claim 1, wherein the disease or disorder is atherosclerosis, dyslipidemia, diabetes.

11. The method of claim 10 wherein the disease or disorder is atherosclerosis.

12. The method of claim 10 wherein the disease or disorder is diabetes.

13. A composition comprising at least one compound of claim 4 and one or more pharmaceutically acceptable carriers.

14. The composition of claim 13 further comprising at least one additional therapeutic agent.

* * * * *